US011807891B2

(12) United States Patent
Senaratne et al.

(10) Patent No.: US 11,807,891 B2
(45) Date of Patent: *Nov. 7, 2023

(54) CARBON MONOXIDE AND CARBON DIOXIDE BIOCONVERSION PROCESS

(71) Applicant: Jupeng Bio, Inc., League City, TX (US)

(72) Inventors: Ryan H Senaratne, Fayetteville, AR (US); Nestor A Camargo, Fayetteville, AR (US); Ryan M Lacey, Fayetteville, AR (US); Abel J Price, Fayetteville, AR (US); Brandon L Beard, Fayetteville, AR (US)

( * ) Notice: Subject to any disclaimer, the term of this patent is extended or adjusted under 35 U.S.C. 154(b) by 785 days.

This patent is subject to a terminal disclaimer.

(21) Appl. No.: 16/530,502

(22) Filed: Aug. 2, 2019

(65) Prior Publication Data

US 2020/0071734 A1    Mar. 5, 2020

Related U.S. Application Data

(60) Provisional application No. 62/741,797, filed on Oct. 5, 2018, provisional application No. 62/741,871, filed on Oct. 5, 2018, provisional application No. 62/716,083, filed on Aug. 8, 2018, provisional application No. 62/716,071, filed on Aug. 8, 2018, provisional application No. 62/716,053, filed on Aug. 8, 2018.

(51) Int. Cl.
   *C12P 7/54*    (2006.01)
   *C12P 7/52*    (2006.01)

(52) U.S. Cl.
   CPC .. *C12P 7/54* (2013.01); *C12P 7/52* (2013.01)

(58) Field of Classification Search
   CPC .... Y02E 50/10; C12P 7/54; C12P 7/52; C12P 7/40
   See application file for complete search history.

(56) References Cited

U.S. PATENT DOCUMENTS

| | | | |
|---|---|---|---|
| 7,285,402 | B2 | 10/2007 | Gaddy et al. |
| 8,293,509 | B2 | 10/2012 | Simpson et al. |
| 10,036,045 | B2 | 7/2018 | Muller et al. |
| 2010/0227377 | A1* | 9/2010 | Adams ............ C12P 7/08 435/252.1 |
| 2016/0040192 | A1 | 2/2016 | Scott et al. |
| 2016/0251683 | A1 | 9/2016 | Tracy et al. |
| 2019/0153488 | A1 | 5/2019 | Stephanopoulous et al. |
| 2019/0211302 | A1 | 7/2019 | Bruno-Barcena et al. |

FOREIGN PATENT DOCUMENTS

| | | | |
|---|---|---|---|
| KR | 1020180077972 | A | 7/2018 |
| WO | 2014202965 | A1 | 12/2014 |
| WO | 2016070160 | A1 | 5/2016 |
| WO | 2017205363 | A1 | 11/2017 |
| WO | 2017210296 | A1 | 12/2017 |

OTHER PUBLICATIONS

Tremblay et al., The Rnf Complex of Clostridium ljungdahlii Is a Proton-Translocating Ferredoxin:NAD Oxidoreductase Essential for Autotrophic Growth, mBio, vol. 4, p. 1-8 (Year: 2012).*
Acharya et al., "Ethanol Production by Syngas Fermentation in a Continuous Stirred Tank Bioreactor Using Clostridium ljungdahlii", Biofuels, 10:2, 221-237, May 16, 2017.
Balch et al., "*Acetobacterium*, a New Genus of Hydrogen-Oxidizing, Carbon Dioxice-Reducing, Anaerobic Bacteria", International Journal of Systematic Baceteriology, vol. 27, No. 4, pp. 355-361, Oct. 1977.
Bertsch et al., "CO Metabolism in the Acetogen Acetobacterium woodii", Appl. Enviorn. Microbiol. 81:5949-5956, Jun. 19, 2015.
Buschhorn et al., "Production and Utilization of Ethanol by the Homoacetogen Acetobacterium woodii", Applied and Environmental Microbiology, vol. 55, No. 7, pp. 1835-1840, Jul. 1989.
Ceccaldi et al., "The Hydrogen Dependent CO2 Reductase: The First Completely CO tolerant FEFE-hydrogenase", Energy Environ. Sci. 2017, 10, 503, Oct. 24, 2016.
Groher et al., "Comparative Reaction Engineering Analysis of different Acetogenic Bacteria for Gas Fermentation", Journal of Biotechnology 228(2016): 82-89.
Haas et al., "Technical Photosynthesis Involving CO2 Electrolysis and Fermentation", Nature Catalysis, vol. 1, pp. 32-33, Jan. 2018.
Humphreys et al. "Advances in Metabolic Engineering in the Microbial Production of Fuels and Chemicals from C1 Gas", Current Opinion in Biotechnology 2018, 50:174-181.
Imkamp et al., "Chemisomotic Energy Conservation with Na$^+$ as the Coupling Ion during Hydrogen-Dependent Caffeate Reduction by Acetobacterium woodii", Journal of Bacteriology, vol. 184, No. 7, pp. 1947-1951, Apr. 2002.
Jones et al., "CO2 Fixation by Anaerobic Non-Photosynthetic Mixotrophy for Improved Carbon Conversion", Nature Communications 7:1280, DOI: 10.1038/ncomms1800, Sep. 30, 2016.
Lehtinen et al., "Production of Alkanes from CO2 by Engineered Bacteria", Biotechnol Biofuels (2018) 11:228.
Mayer et al., "Carbon Monoxide Conversion with Clostridium aceticum", Biotechnology and Bioengineering 2018:115:2740-2750.
Mourato et al., "A Continuous System for Biocatalytic Hydrogenation CO2 to Formate", Bioresource Technology 255(2017):149-156.
Muller, "Energy Conservation in Acetogenic Bacteria", Applied and Environmental Microbiology, vol. 69, No. 11, pp. 6345-6353, Nov. 2003.
Muller, "New Horizons in Acetogenic Conversion of One-Carbon Substrates and Biological Hydrogen Storage", Trends in Biotechnology XP-0027940231 (2019).

(Continued)

*Primary Examiner* — Taeyoon Kim
*Assistant Examiner* — Tiffany M Gough
(74) *Attorney, Agent, or Firm* — Mengqi Zheng; James P. Krueger

(57) ABSTRACT

A process is provided for bioconversion of carbon monoxide and carbon dioxide. More specifically, the process includes fermenting carbon monoxide and carbon dioxide containing substrate with acetogenic bacteria. The process provides for high levels of carbon monoxide and carbon dioxide conversions and utilization of hydrogen.

21 Claims, 13 Drawing Sheets

(56) References Cited

OTHER PUBLICATIONS

Poehlein et al., "An Ancient Pathway Combining Carbon Dioxide Fixation with the Generation and Utilization of a Sodium Ion Gradient for ATP Synthesis", PLoS One 7(3): e33439. doi:10.1371/journal.pone.0033439, Mar. 29, 2012.

Rowaihi et al., "A Two-Stage Biological Gas to Liquid Transfer Process to Convert Carbon Dioxide into Bioplastic", Bioresource Technology Reports 1 (2018) 61-68.

Takora et al., "Using Gas Mixtures of CO, CO2 and H2 as Microbial Substrates: the Do's and Don'ts of Successful Technology Transfer from Laboratory to Production Scale", Microbial Biotechnology 11, 506-625 (2018).

Valgepea et al. "H2 Drives Metabolic Rearrangements in Gas-Fermenting Clostridium autoethanogenum", Biotechnol. Biofuels (2018) 11:55.

Weuster-Botz, "Chemicals from CO2: Hydrogenotrophic Protection of Acetate with Acetobacterium woodii", Dechema, 2013, https://dechema.de/events_media/Veranstaltungen/2013/Irsee_Analytics_2013/Session+Heterogene+biotechnische+Systeme-p-5242.pdf.

Yu et al., "Efficient Reduction of CO2 by the Molybdenum-Containing Formate Dehydrogenase from Cupriavidus necator (*Ralstonia eutropha*)", J. Biol. Chem. (2017) 292(41) 16872-16879.

\* cited by examiner

CARBON MONOXIDE AND CARBON DIOXIDE BIOCONVERSION PROCESS

This application claims the benefit of U.S. Provisional Application Nos. 62/716,083, filed Aug. 8, 2018, 62/716,071, filed Aug. 8, 2018, 62/716,053, filed Aug. 8, 2018, 62/741,871, filed Oct. 5, 2018, and 62/741,797, filed Oct. 5, 2018, all of which are incorporated in their entirety herein by reference.

A process is provided for bioconversion of carbon monoxide and carbon dioxide. More specifically, the process includes providing carbon monoxide and carbon dioxide containing gaseous streams to acetogenic bacteria. The process provides for high levels of carbon monoxide and carbon dioxide conversions and utilization of hydrogen.

BACKGROUND

Carbon dioxide and carbon monoxide generation occur from natural processes as well as industrial processes that include combustion of fossil fuels such as coal, oil and natural gas. Due in part to industrial processes, atmospheric carbon dioxide and carbon monoxide concentrations continue to increase. These increases in carbon dioxide and carbon monoxide concentrations may contribute to atmospheric changes which result in climate change and global warming. Carbon dioxide is difficult to utilize in biological processes because of its highly oxidized state.

In addition to carbon dioxide and carbon monoxide, many industrial processes also result in production of hydrogen. Hydrogen has a high level of reducing potential. However, hydrogen is difficult to store and utilize due to its very flammable nature.

In view of the large amount of carbon dioxide and carbon monoxide generated, there is a need for a bacterial fermentation system that can utilize both carbon monoxide and carbon dioxide.

SUMMARY

A process includes providing a gaseous substrate Gx to a bioreactor Bx, the gaseous substrate Gx comprising $CO_2$ and contains about 5 to about 90 mole % $CO_2$. Acetogenic bacteria Mx are provided to the bioreactor Bx. The acetogenic bacteria Mx includes a sodium translocating ATPase that is active during fermentation in the bioreactor Bx. The process includes providing sodium ions to the bioreactor Bx through one or more sodium ion sources and fermenting the gaseous substrate Gx with the acetogenic bacteria Mx in a fermentation broth comprising the acetogenic bacteria Mx and the one or more sodium ion sources to produce one or more organic acids. The fermentation broth includes less than about 0.01 grams per liter yeast extract, less than about 0.01 grams per liter carbohydrate, and wherein the sodium ions are provided with a sodium feed rate of about 290 to about 8750 µg/gram of cells/minute. The process includes maintaining the fermentation broth at a pH in a range of about 4 to about 6.9. At least a portion of the one or more organic acids is provided to a bioreactor Bi. The process further includes providing gaseous substrate Gi to the bioreactor Bi, the gaseous substrate Gi comprising CO and contains about 5 to about 90 mole % CO. Acetogenic bacteria Mi is provided to bioreactor Bi. The acetogenic bacteria Mi includes a proton translocating ATPase that is active during fermentation in the bioreactor Bi. The process further includes fermenting, the gaseous substrate Gi in the bioreactor Bi with the acetogenic bacteria Mi in a fermentation broth comprising the acetogenic bacteria Mi to produce a liquid stream comprising one or more alcohols and a gaseous stream Gp comprising $CO_2$.

A process includes providing a gaseous substrate Gx to a bioreactor Bx, the gaseous substrate Gx comprising $CO_2$ and $H_2$ and contains about 5 to about 90 mole % $CO_2$. Acetogenic bacteria Mx are provided to the bioreactor Bx. The acetogenic bacteria Mx includes a sodium translocating ATPase that is active during fermentation in the bioreactor Bx. The process includes providing sodium ions to the bioreactor Bx through one or more sodium ion sources and fermenting the gaseous substrate Gx with the acetogenic bacteria Mx in a fermentation broth comprising the acetogenic bacteria Mx and the one or more sodium ion sources to produce one or more organic acids. The fermentation broth includes less than about 0.01 grams per liter yeast extract, less than about 0.01 grams per liter carbohydrate and wherein the sodium ions are provided with a sodium feed rate of about 290 to about 8750 µg/gram of cells/minute. The process includes maintaining the fermentation broth at a pH in a range of about 4 to about 6.9. At least a portion of the one or more organic acids is provided to a bioreactor Bi. The process further includes providing gaseous substrate Gi to the bioreactor Bi, the gaseous substrate Gi comprising CO and contains about 5 to about 90 mole % CO. Acetogenic bacteria Mi is provided to bioreactor Bi. The acetogenic bacteria Mi includes a proton translocating ATPase that is active during fermentation in the bioreactor Bi. The process further includes fermenting the gaseous substrate (ii in the bioreactor Bi with the acetogenic bacteria Mi in a fermentation broth comprising the acetogenic bacteria Mi to produce a liquid stream comprising one or more alcohols and a gaseous stream Gp comprising $CO_2$.

A process includes providing a gaseous substrate Gx to a bioreactor Bx, the gaseous substrate Gx comprising $CO_2$ and containing about 5 to about 90 mole % $CO_2$. Acetogenic bacteria Mx are provided to the bioreactor Bx, wherein the acetogenic bacteria Mx includes a sodium translocating ATPase that is active during fermentation in the bioreactor Bx. The process includes providing sodium ions to the bioreactor Bx through one or more sodium ion sources and fermenting the gaseous substrate Gx with the acetogenic bacteria Mx in a fermentation broth comprising the acetogenic bacteria Mx and the one or more sodium ion sources to produce one or more organic acids. The fermentation broth includes less than about 0.01 grams per liter yeast extract, less than about 0.01 grams per liter carbohydrate, and wherein the sodium ions are provided with a sodium feed rate of about 290 to about 8750 µg/gram of cells/minute. The process includes maintaining the fermentation broth at a pH in a range of about 4 to about 6.9. At least a portion of the one or more organic acids to a bioreactor system Bi-s. The process further includes providing a gaseous substrate Gi to the bioreactor system Bi-s, the gaseous substrate Gi comprising CO and containing about 5 to about 90 mole % CO. Acetogenic bacteria Mi to bioreactor system Bi-s, wherein the acetogenic bacteria Mi includes a proton translocating ATPase that is active during fermentation in the bioreactor system Bi-s. The process further includes fermenting the gaseous substrate Gi in the bioreactor system Bi-s with the acetogenic bacteria Mi in a fermentation broth, comprising the acetogenic bacteria Mi to produce a liquid stream comprising one or more alcohols and a gaseous stream Gp comprising $CO_2$.

BRIEF DESCRIPTION OF FIGURES

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

DETAILED DESCRIPTION

Figure 1:
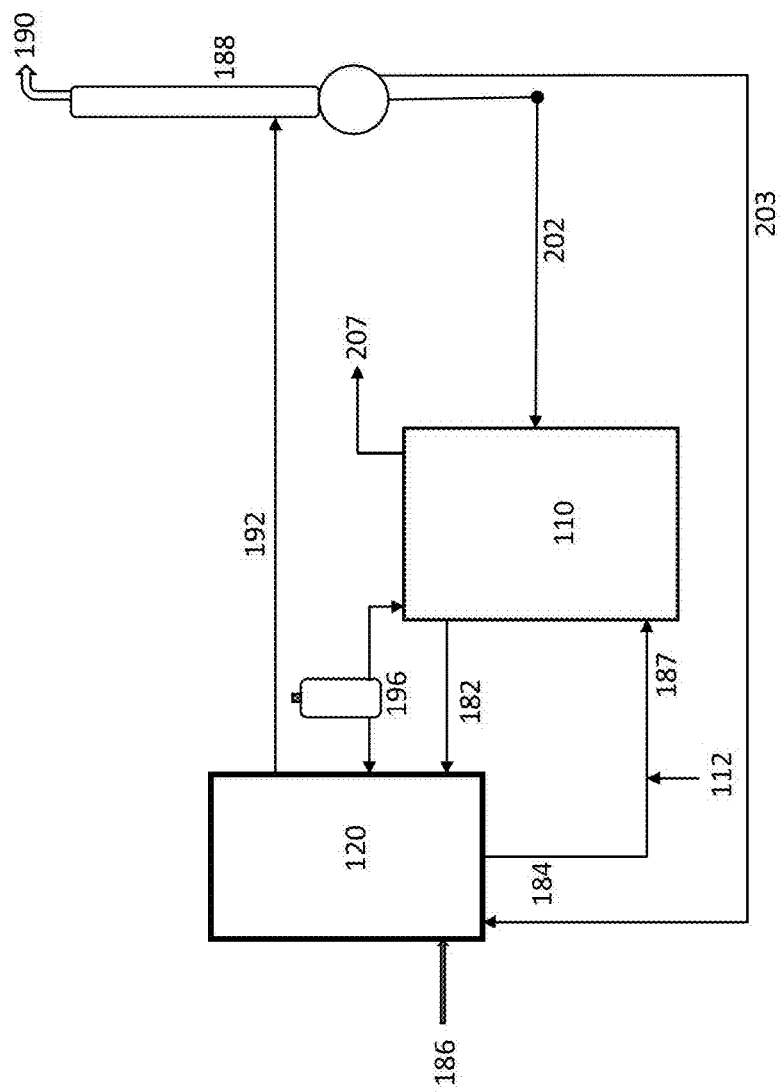
FIG. 1 illustrates a schematic of a system for producing one or more oxygenated hydrocarbonaceous compounds from a fermentation process using two bioreactors.

The following description is not to be taken in a limiting sense, but is made merely for the purpose of describing the general principles of exemplary embodiments. The scope of the disclosure should be determined with reference to the claims.

Definitions

Unless otherwise defined, the following terms as used throughout this specification for the present disclosure are defined as follows and can include either the singular or plural forms of definitions below defined:

The term "about" modifying any amount refers to the variation in that amount encountered in real world conditions, e.g., in the lab, pilot plant, or production facility. For example, an amount of an ingredient or measurement employed in a mixture or quantity when modified by "about" includes the variation and degree of care typically employed in measuring in an experimental condition in production plant, or lab. For example, the amount of a component of a product when modified by "about" includes the variation between batches in multiple experiments in the plant or lab and the variation inherent in the analytical method. Whether or not modified by "about," the amounts include equivalents to those amounts. Any quantity stated herein and modified by "about" can also be employed in the present disclosure as the amount not modified by "about".

The term "fermentor" includes a fermentation device/ bioreactor consisting of one or more vessels and/or towers or piping arrangements, which includes a batch reactor, semi-batch reactor, continuous reactor, continuous stirred tank reactor (CSTR), bubble column reactor, external circulation loop reactor, internal circulation loop reactor, immobilized cell reactor (ICR), tickle bed reactor (TBR), moving bed biofilm reactor (MBBR), gas lift reactor, membrane reactor such as hollow fibre membrane bioreactor (HFMBR), static mixer, gas lift fermentor, or other vessel or other device suitable for gas-liquid contact.

The terms "fermentation", fermentation process" or "fermentation reaction" and the like are intended to encompass both, the growth phase and product biosynthesis phase of the process. In one aspect, fermentation refers to conversion of $CO_2$ to acetic acid. In another aspect, fermentation refers to conversion of CO to alcohol.

The term "cell density" means mass of microorganism cells per unit volume of fermentation broth, for example, grams/liter.

The term "specific $CO_2$ uptake" means an amount of CO in mmoles consumed by unit mass of microorganism cells (g) per unit time in minutes, i.e. mmole/gram/minute. The term "specific CO uptake" means an amount of CO in mmoles consumed by unit mass of microorganism cells (g) per unit time in minutes, i.e. mmole/gram/minute.

As used herein, productivity is expressed as STY. In this aspect, alcohol productivity may be expressed as STY (space time yield expressed as g ethanol/(L·day) or (g acetic acid/(L·day).

As used herein, "oxygenated hydrocarbonaceous compounds" may include carbon hydrogen and oxygen containing compounds, such as for example, ethanol and butanol.

CO/$CO_2$ Conversion System

Embodiments of the disclosure provide methods, systems, and compositions for producing and obtaining alcohol products and bacterial proteins derived from microbial cell biomass after an anaerobic bacterial fermentation process. In one embodiment, a system and a method of increasing carbon capture efficiency reducing carbon dioxide footprint, and increasing alcohol product productivity are provided.

As shown in FIG. 1, the system may include bioreactor Bi 120 being adapted to ferment a gaseous substrate Gi 186 with an acetogenic bacteria Mi. The gaseous substrate Gi 186 may include carbon monoxide (CO) and hydrogen gas ($H_2$).

In one aspect, the fermentation of gaseous substrate Gi 186 in bioreactor Bi 120 results in a gaseous stream Gp 184. Gaseous stream Gp 184 comprises carbon dioxide ($CO_2$) and may include one or more gases selected from the group consisting of carbon monoxide (CO), hydrogen gas ($H_2$), methane ($CH_4$), nitrogen ($N_2$) and combinations thereof. In this aspect, the gaseous stream Gp from bioreactor Bi 120 may include about 0.5 mole % to about 50 mole % CO, in another aspect, about 0.5 mole % to about 40 mole %, in another aspect, about 0.5 mole % to about 30 mole %, in another aspect, about 0.5 mole % to about 20 mole %, and in another aspect, about 0.5 mole % to about 10 mole % CO. Further, in another aspect, the gaseous stream Gp from bioreactor Bi 120 may include about 5 mole % to 100 mole % $CO_2$, in still another aspect, about 5 mole % to 90 mole % $CO_2$, in another aspect, 5 mole % to 80 mole % $CO_2$, in another aspect, 5 mole % to 70 mole % $CO_2$, in another aspect, 5 mole % to 60 mole % $CO_2$, in another aspect, 5 mole % to 50 mole % $CO_2$, in another aspect, 5 mole % to 40 mole % $CO_2$, in another aspect, 5 mole % to 30 mole % $CO_2$, in another aspect, 5 mole % to 20 mole % $CO_2$, and in another aspect, 5 mole % to 10 mole % $CO_2$.

As shown in FIG. 1, the system may include a bioreactor Bx 110 adapted to ferment a gaseous substrate with an acetogenic bacteria Mx. Gaseous substrate Gx is provided to bioreactor Bx 110 at gas line 187. In this aspect, gaseous stream Gp 184 from bioreactor Bi 120 may be provided directly to bioreactor Bx 110. In another aspect, the system may include gas supplementation line 112 to provide additional gaseous substrate which is blended with gaseous stream Gp 184 to provide gaseous stream Gx 187 which is conveyed into bioreactor Bx 110. Off-gas from bioreactor Bx 110 may be vented through vent line 207. Both bioreactors are supplied with nutrient from nutrient supply tank 196. Nutrient supply tank 196 may include multiple subunits to supply the same or different nutrients to each bioreactor.

In addition, the system may also include a fluid line 182 connecting bioreactor Bx 110 to bioreactor Bi 120 to deliver one or more acid compounds from bioreactor 110 Bx to bioreactor Bi 120. The one or more acid compounds generated from bioreactor Bx 110 include C1 to C10 organic acids. Examples of C1 to C10 organic acids include acetic acid, formic acid, propionic acid, butyric acid, pentanoic (valeric acid) hexanoic acid, heptanoic acid, decanoic acid and combinations thereof. In one aspect, the acid compound from bioreactor Bx 110 that is delivered to bioreactor Bi 120 is effective for increasing alcohol production in bioreactor Bi 120. In an aspect where the organic acid is acetic acid, gaseous substrate Gi 186 is provided to bioreactor Bi 120 to maintain an acetic acid concentration of about 5 g/L or less in bioreactor Bi 120. When gaseous substrate Gi is provided to lower the concentration of acetic acid, a concentration of butyric acid is also lowered. Therefore, acetic acid is used as a marker to maintain appropriate amounts of organic acids in bioreactor Bi. In another aspect, the organic acid feed rate is used to keep an acetic acid concentration of about 5 or less in bioreactor Bi 120.

As further illustrated in FIG. 1, cell permeate line 192 is configured to deliver permeate to a distillation tower 188 for separation of product 190 from permeate. Product may include an alcohol-containing product that comprises ethanol, butanol, and combinations thereof. Water (distillation bottoms) may be returned to bioreactor Bx 110 through water return line 202 and/or to bioreactor Bi 120 through water return line 203.

Figure 2:
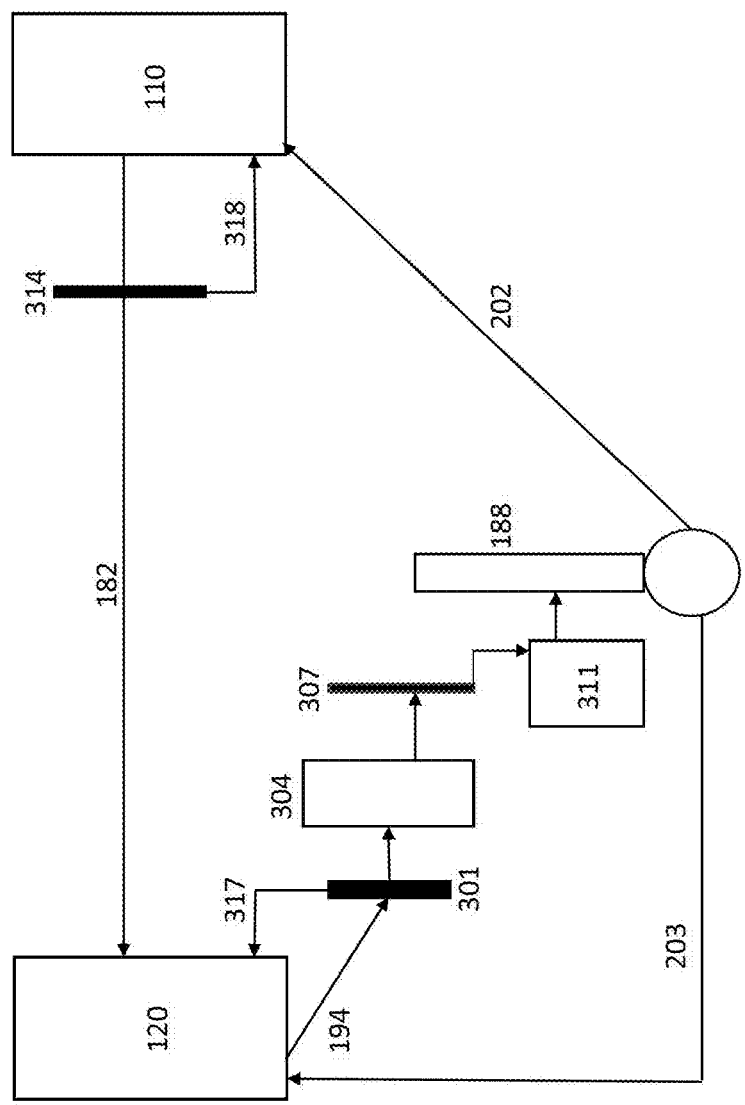
FIG. 2 illustrates a schematic of a water recycle system.

FIG. 2 illustrates a more detailed aspect of a water recycle system. In this aspect, organic acid produced in bioreactor Bx 110 is conveyed through micro filtration 314 and further provided to bioreactor Bi 120 through fluid line 182. At least a portion of cells may be returned from microfiltration 314 to bioreactor Bx 110 by cell recycle line 318. Broth from bioreactor Bi 120 is conveyed through line 194 to microfiltration 301. At least a portion of cells may be returned from microfiltration 301 to bioreactor Bi 120 by cell recycle line 317. In some optional aspect, liquid from line 194 may go to ultrafiltration 307 and at least a portion of cells may be returned from ultrafiltration 307 to bioreactor Bi 120. Liquid from ultrafiltration 307 is sent to distillation feed tank 311 and then to distillation tower 188. Water (distillation bottoms) may be returned to bioreactor Bx 110 through water return line 202 and/or to bioreactor Bi 120 through water return line 203.

Figure 3:
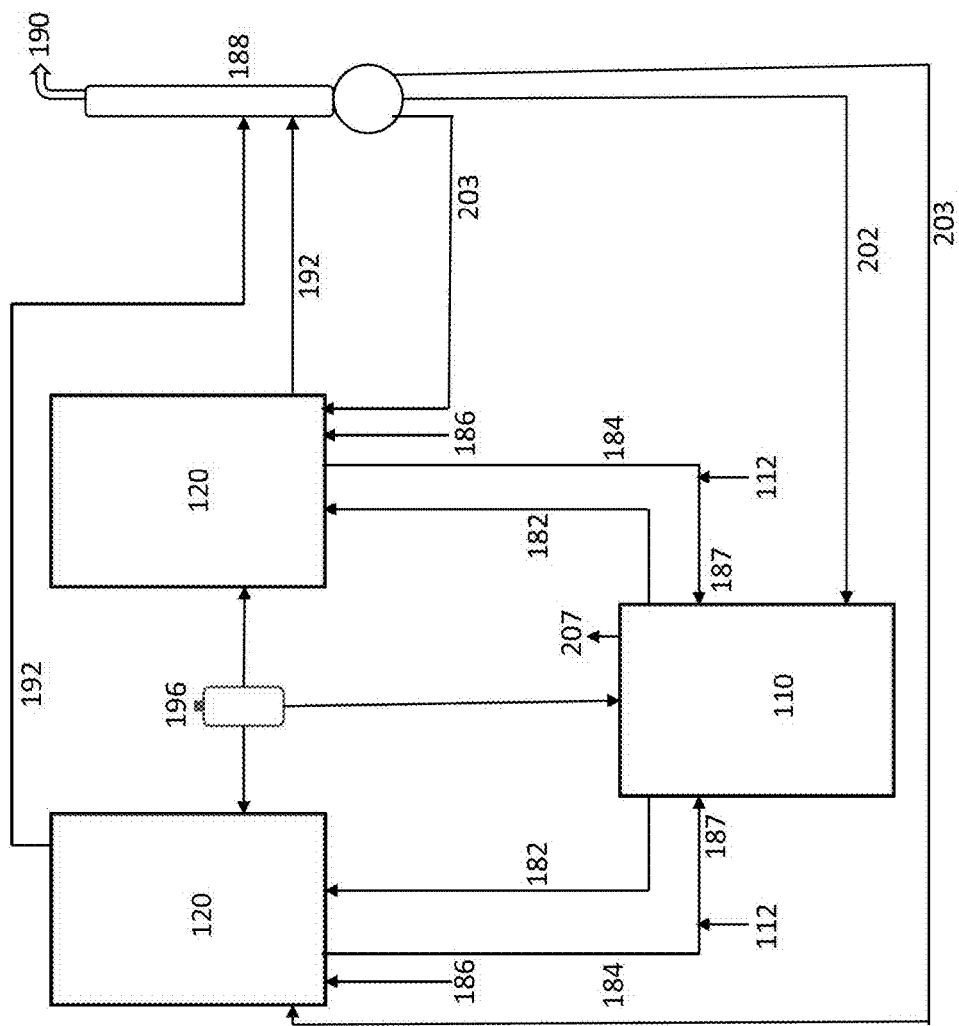
FIG. 3 shows a schematic of a system for producing one or more oxygenated hydrocarbonaceous compounds from a fermentation process using multiple bioreactors.

In another aspect, as shown in FIG. 3, a process may include bioreactor Bx 110 being adapted to ferment a gaseous substrate Gx 187 with an acetogenic bacteria Mx. The gaseous substrate Gx 187 may include carbon monoxide (CO) and hydrogen gas ($H_2$) in addition to $CO_2$. As shown in FIG. 3, gaseous substrate Gx may be supplied to bioreactor Bx from bioreactor system Bi-s, which include two or more bioreactors Bi-n. As shown in FIG. 3, Bi-n includes two bioreactors Bi 120.

Gaseous substrate Gx 187 is provided to bioreactor Bx 110 at one or more gas lines. In this aspect, gaseous stream Gp 184 from the two or more bioreactors Bi 120 of bioreactor system Bi-s may be provided directly to bioreactor Bx 110. In another aspect, the system may include gas supplementation lines 112 to provide additional gaseous substrate which is blended with gaseous stream Gp 184 to provide gaseous stream Gx 187 which is conveyed into bioreactor Bx 110. Off-gas from bioreactor Bx 110 may be vented through vent line 207. Each bioreactor may be supplied with nutrient from nutrients from one or more supply tank 196. Nutrient supply tank 196 may include multiple subunits to supply the same or different nutrients to each bioreactor.

The bioreactor system Bi-s may include two or more bioreactors Bi 120 being adapted to ferment a gaseous substrate Gi 186 with an acetogenic bacteria Mi. The gaseous substrate Gi 186 may include carbon monoxide (CO) and hydrogen gas ($H_2$). The fermentation of gaseous substrate Gi 186 in the bioreactors Bi 120 of bioreactor system Bi-s results in one or more gaseous streams Gp 184. Gaseous stream Gp 184 comprises carbon dioxide ($CO_2$) and may include one or more gases selected from the group consisting of carbon monoxide (CO), hydrogen gas ($H_2$), methane ($CH_4$), nitrogen ($N_2$), and combinations thereof. In this aspect, the gaseous stream Gp from bioreactor Bi 120 may include about 0.5 mole % to about 50 mole % CO, in another aspect, about 0.5 mole % to about 40 mole %, in another aspect, about 0.5 mole % to about 30 mole %, another aspect, about 0.5 mole % to about 20 mole %, and in another aspect, about 0.5 mole % to about 10 mole % CO, Further, in another aspect, the gaseous stream Gp from bioreactor Bi 120 may include about 5 mole % to 100 mole % $CO_2$, in still another aspect, about 5 mole % to 90 mole % $CO_2$, in another aspect, 5 mole % to 80 mole % $CO_2$, in another aspect, 5 mole % to 70 mole % $CO_2$, in another aspect, 5 mole % to 60 mole % $CO_2$, in another aspect, 5 mole %0 to 50 mole % $CO_2$, in another aspect, 5 mole % to 40 mole % $CO_2$, in another aspect, 5 mole % to 30 mole % $CO_2$, in another aspect, 5 mole % to 20 mole % $CO_2$, and in another aspect, 5 mole % to 10 mole % $CO_2$. In one aspect the gaseous substrate Gi 186 is provided to the two or more bioreactors Bi 120 (collectively referred to as Bi-n) to achieve a superficial gas velocity effective for producing about 10% or less of a culture volume to foam per hour.

In addition, the system may also include two or more fluid lines 182 connecting bioreactor Bx 110 to bioreactor system Bi-s to deliver one or more acid compounds from bioreactor Bx 110 to bioreactor system Bi-s. In this aspect, bioreactor system Bi-s may include two or more bioreactors Bi 120 (two bioreactors Bi 120 are shown). The one or more acid compounds generated from bioreactor Bx 110 include C1 to C10 organic acids. Examples of C1 to C10 organic acids include acetic acid, formic acid, propionic acid, butyric acid, pentanoic (valeric acid) hexanoic acid, heptanoic acid, decanoic acid and combinations thereof. In one aspect, the acid compound from bioreactor Bx 110 that is delivered to bioreactor system Bi-s is effective for increasing alcohol production in bioreactor system Bi-s.

As further illustrated in FIG. 3, cell permeate lines 192 are configured to deliver permeate to a distillation tower 188 for separation of product 190. Product may include an alcohol-containing product that comprises ethanol, butanol, and combinations thereof. Water (distillation bottoms) may be returned to bioreactor Bx 110 through water return line 202 and/or to bioreactors Bi 120 through water return lines 203.

Bioreactor Bi for CO Conversion

CO-Containing Substrate: A CO-containing substrate (described as gaseous substrate Gi 186) may include any gas that includes CO. In this aspect, a CO-containing gas may include syngas, industrial gases, and mixtures thereof. In a related aspect, a gaseous substrate provided to bioreactor Bi 120 may include in addition to CO, nitrogen gas ($N_2$), carbon dioxide ($CO_2$), methane gas ($CH_4$), syngas, and combinations thereof.

Syngas may be provided from any known source. In one aspect, syngas may be sourced from gasification of carbonaceous materials. Gasification involves partial combustion of biomass in a restricted supply of oxygen. The resultant gas may include CO and $H_2$. In this aspect, syngas will contain at least about 10 mole % CO, in one aspect, at least about 20 mole %, in one aspect, about 10 to about 100 mole %, in another aspect, about 20 to about 100 mole % CO, in another aspect, about 30 to about 90 mole % CO, in another aspect, about 40 to about 80 mole % CO, and in another aspect, about 50 to about 70 mole % CO. Some examples of suitable gasification methods and apparatus are provided in U.S. Ser. No. 61/516,667, 61/516,704 and 61/516,646, all of which were filed on Apr. 6, 2011, and in U.S. Ser. Nos. 13/427,144, 13/427,193 and 13/427,247, all of which were filed on Mar. 22, 2012, and all of which are incorporated herein by reference.

In another aspect, the process has applicability to supporting the production of alcohol from gaseous substrates such as high volume CO-containing industrial gases. In some aspects, a gas that includes CO is derived from carbon containing waste, for example, industrial waste gases or from the gasification of other wastes. As such, the processes represent effective processes for capturing carbon that would otherwise be exhausted into the environment. Examples of industrial gases include gases produced during ferrous metal products manufacturing, non-ferrous products manufacturing, petroleum refining processes, gasification of coal, gasification of biomass, electric power production, carbon black production, ammonia production, methanol production, coke manufacturing and gas reforming.

In another aspect, $H_2$ may be supplied from industrial waste gases or from the gasification of other wastes. As such, the processes represent effective processes for capturing hydrogen that would otherwise be exhausted into the environment. Examples of industrial gases include gases produced during ferrous metal products manufacturing, non-ferrous products manufacturing, petroleum refining processes, gasification of coal, gasification of biomass, electric power production, carbon black production, ammonia production, methanol production and coke manufacturing. Other sources of hydrogen may include for example, $H_2O$ electrolysis and bio-generated $H_2$.

Depending on the composition of the CO-containing substrate, the CO-containing substrate may be provided directly to a fermentation process or may be further modified to include an appropriate $H_2$ to CO molar ratio. In one aspect, CO-containing substrate provided to the fermentor has an $H_2$ to CO molar ratio of about 0.2 or more, in another aspect, about 0.25 or more, and in another aspect, about 0.5 or more. In another aspect, CO-containing substrate provided to the fermentor may include about 40 mole percent or more CO plus $H_2$ and about 30 mole percent or less CO, in another aspect, about 50 mole percent or more CO plus $H_2$ and about 35 mole percent or less CO, and in another aspect, about 80 mole percent or more CO plus $H_2$ and about 20 mole percent or less CO.

In one aspect, the CO-containing substrate includes CO and $H_2$. In this aspect, the CO-containing substrate will contain at least about 10 mole % CO, in one aspect, at least about 20 mole %, in one aspect, about 10 to about 100 mole in another aspect, about 20 to about 100 mole % CO, in another aspect, about 30 to about 90 mole % CO, in another aspect, about 40 to about 80 mole % CO, and in another aspect, about 50 to about 70 mole % CO.

In one aspect, a gas separator is configured to substantially separate at least one portion of the gas stream, wherein the portion includes one or more components. For example, the gas separator may separate $CO_2$ from a gas stream comprising the following components: CO, $CO_2$, $H_2$, wherein the $CO_2$ may be passed to $CO_2$ storage and the remainder of the gas stream (comprising CO and $H_2$) may be passed to a bioreactor. Any gas separator known in the art may be utilized. In this aspect, syngas provided to the fermenter will have about 10 mole % or less $CO_2$, in another aspect, about 1 mole % or less $CO_2$, and in another aspect, about 0.1 mole % or less $CO_2$.

Certain gas streams may include a high concentration of CO and low concentrations of $H_2$. In one aspect, it may be desirable to optimize the composition of the substrate stream in order to achieve higher efficiency of alcohol production and/or overall carbon, capture. In another aspect, the concentration of $H_2$ in the substrate stream may be increased before the stream is passed to the bioreactor.

According to particular aspects of the disclosure, streams from two or more sources can be combined and/or blended to produce a desirable and/or optimized substrate stream. For example, a stream comprising a high concentration of CO, such as the exhaust from a steel mill converter, can be combined with a stream comprising high concentrations of $H_2$, such as the off-gas from a steel mill coke oven.

Depending, on the composition of the gaseous CO-containing substrate, it may also be desirable to treat it to remove any undesired impurities, such as dust particles before introducing it to the fermentation. For example, the gaseous substrate may be filtered or scrubbed using known methods.

Bioreactor Design and Operation: Descriptions of fermentor designs are described in U.S. Ser. Nos. 13/471,827 and 13/471,858, both filed May 15, 2012, and U.S. Ser. No. 13/473,167, filed May 16, 2012, all of which are incorporated herein by reference.

In accordance with one aspect, the fermentation process is started by addition of medium to the reactor vessel. Some examples of medium compositions are described in U.S. Ser. Nos. 61/650,098 and 61/650,093, filed May 22, 2012, and in U.S. Pat. No. 7,285,402, filed Jul. 23, 2001, all of which are incorporated herein by reference. The medium may be sterilized to remove undesirable microorganisms and the reactor is inoculated with the desired microorganisms. Sterilization may not, always be required.

Concentrations of various medium components for use in bioreactor Bi 120 with acetogenic bacteria Mi are as follows:

| Element | Concentration mg/L | Feed Rate µg/gram cells/min |
| --- | --- | --- |
| $NH_4^+$ | 164-6560 | 41-1640 |
| Fe | 1.7-68 | 0.425-17 |
| Ni | 0.07-2.81 | 0.017-0.702 |
| Co | 0.037-1.49 | 0.009-0.373 |
| Se | 0.027-1.1 | 0.006-0.274 |

| Element | Concentration mg/L | Feed Rate µg/gram cells/min |
| --- | --- | --- |
| Zn | 0.116-4.64 | 0.198-5.95 |
| W | 0.8-32.1 | 0.26-8.03 |
| K | 39-1573 | 9.83-393.25 |
| Mg | 1.4-57.3 | 0.35-14.32 |
| S | 15-625 | 3.9-156.2 |
| P | 15-601 | 3.76-150.43 |
| d-biotin | 0.016-0.64 | 0.004-0.16 |
| thiamine HCl | 0.04-1.6 | 0.01-0.4 |
| calcium-D-pantothenate | 0.02-0.81 | 0.005-0.202 |

The ability of certain acetogens to utilize CO is due in part to the presence of a proton or hydrogen pump, also referred to as a proton translocating ATPase. Both proton translocating ATPase and sodium translocating ATPase are described in Muller, "Energy Conservation in Acetogenic Bacteria," Appl. Environ. Microbiol. November 2003, vol. 69, no. 11, pp. 6345-6353, which is incorporated herein by reference. The term proton translocating ATPase may be used interchangeably with the term proton dependent ATPase and the term sodium translocating ATPase may be used interchangeably with the term sodium dependent ATPase. Hence, in one aspect, the process includes conducting fermentations in the fermentation bioreactor with acetogenic bacteria Mi that include a proton translocating ATPase. Examples of useful acetogenic bacteria Mi include those of the genus *Clostridium*, such as strains of *Clostridium ljungdahlii*, including those described in WO 2000/68407, EP 117309, U.S. Pat. Nos. 5,173,429, 5,593,886 and 6,368,819, WO 1998/00558 and WO 2002/08438, strains of *Clostridium autoethanogenum* (DSM 10061 and DSM 19630 of DSMZ, Germany) including those described in WO 2007/117157 and WO 2009/151342 and *Clostridium ragsdalei* (P11, ATCC BAA-622) and *Alkalibaculum bacchi* (CP11, ATCC BAA-1772) including those described respectively in U.S. Pat. No. 7,704,723 and "Biofuels and Bioproducts from Biomass-Generated Synthesis Gas", Hasan Atiyeh, presented in Oklahoma EPSCoR Annual State Conference, Apr. 29, 2010 and *Clostridium carboxidivorans* (ATCC PTA-7827) described in U.S. Patent Application No. 2007/0276447. Other suitable microorganisms includes those of the genus *Moorella*, including *Morella* sp. HUC22-1, and those of the genus *Carboxydothermus*. Each of these references is incorporated herein by reference. Mixed cultures of two or more microorganisms may be used.

Additional examples of useful acetogenic bacteria Mi include *Acetogenium kivui*, *Acetoanaerobium noterae*, *Acetobacterium woodii*, *Alkalibaculum bacchi* CP11 (ATCC BAA-1772), *Blautia producta*, *Butyribacterium methylotrophicum*, *Caldanaerobacter subterraneous*, *Caldanaerobacter subterraneous pacificus*, *Carboxydothermus hydrogenoformans*, *Clostridium aceticum*, *Clostridium acetobutylicum*, *Clostridium acetobutylicum* P262 (DSM 19630 of DSMZ Germany), *Clostridium autoethanogenum* (DSM 19630 of DSMZ Germany), *Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Clostridium carboxidivorans* P7 (ATCC PTA-7827), *Clostridium coskatii* (ATCC PTA-10522), *Clostridium drakei*, *Clostridium ljungdahlii* PETC (ATCC 49587), *Clostridium ljungdahlii* ERI2 (ATCC 55380), *Clostridium ljungdahlii* C-01 (ATCC 55988), *Clostridium ljungdahlii* O-52 (ATCC 55889), *Clostridium magnum*, *Clostridium pasteurianum* (DSM 525 of DSMZ Germany), *Clostridium ragsdalei* P11 (ATCC BAA-622), *Clostridium scatologenes*, *Clostridium thermoaceticum*, *Clostridium ultunense*, *Desulfotomaculum kuznetsovii* *Eubacterium limosum*, *Geobacter sulfurreducens*, *Methanosarcina acetivorans*, *Methanosarcina barkeri*, *Moorella thermoacetica*, *Moorella thermoautotrophica*, *Oxobacter pfennigii*, *Peptostreptococcus productus*, *Ruminococcus productus*, *Thermoanaerobacter kivui*, *Clostridium Stick-landii*, and mixtures thereof.

The fermentation should desirably be carried out under appropriate conditions for the desired fermentation to occur (e.g. CO-to-ethanol). Reaction conditions that should be considered include pressure, temperature, gas flow rate, liquid flow rate, medium pH, medium redox potential, agitation rate (if using a stirred tank reactor), inoculum level, maximum gas substrate concentrations to ensure that CO in the liquid phase does not become limiting, and maximum product concentrations to avoid product inhibition.

Startup: Upon inoculation, an initial feed gas supply rate is established effective for supplying the initial population of microorganisms. Effluent gas is analyzed to determine the content of the effluent gas. Results of gas analysis are used to control feed gas rates. In this aspect, the process provides a calculated CO quantities (mmoles) to initial cell density (grams/liter) ratio of about 0.2 to about 0.9, in another aspect, about 0.5 to about 0.9, in another aspect, about 0.6 to about 0.8, in another aspect, about 0.5 to about 0.7, in another aspect, about 0.2 to about 0.5, and in another aspect, about 0.5 to about 0.6.

In another aspect, a fermentation process includes providing syngas to a fermentation medium in an amount effective for providing an initial calculated CO concentration in the fermentation broth of about 0.05 mM to about 0.10 mM, in another aspect, about 0.15 mM to about 0.50 mM, in another aspect, about 0.15 mM to about 0.35 mM, in another aspect, about 0.20 mM to about 0.30 mM, and in another aspect, about 0.23 mM to about 0.27 mM. Dissolved CO was calculated using Henry's law and the kLa of the reactor. The process is effective for increasing cell density as compared to a starting cell density.

As used herein, target cell density means a cell density of about to about 2.0 grams/liter or more, in another aspect, about 2 to about 30 grams/liter, in another aspect, about 2 to about 25 grams/liter, in another aspect, about 2 to about 20 grains/liter, in another aspect, about 2 to about 10 grams/liter, in another aspect, about 2 to about 8 grams/liter, in another aspect, about 3 to about 30 grams/liter, in another aspect, about 3 to about 6 grams/liter, and in another aspect, about 4 to about 5 grains/liter.

Post-startup: Upon reaching desired levels, liquid phase and cellular material is withdrawn from the reactor and replenished with medium. In post-startup, cell density will remain at constant levels.

Bioreactor Bx for $CO_2$ Conversion $CO_2$-Containing Substrate: In one aspect, the process includes providing a $CO_2$-containing gaseous substrate (described as gaseous substrate Gx 187) to a bioreactor. A $CO_2$-containing substrate may include any gas that includes $CO_2$. In this aspect, a $CO_2$-containing gas may include industrial gases, fermentor gas streams including for example, fermentor off-gases and mixtures thereof. In a related aspect, the $CO_2$-containing substrate may include hydrogen or it may be blended with a hydrogen source to provide desired levels and ratios of $H_2$ to $CO_2$.

Industrial gases: In one aspect, the process includes providing a $CO_2$-containing substrate to a bioreactor where the $CO_2$-containing substrate is generated from industrial gases. Some examples of industrial gases include steel mill gas, industrial gas and incinerator exhaust gas. Examples of industrial gases include gases produced during ferrous metal products manufacturing, non-ferrous products manufacturing, petroleum refining processes, gasification of coal, gasification of biomass, electric power production, carbon black production, ammonia production, methanol production and coke manufacturing. Sources of hydrogen may include fossil fuels, steam reforming, oxidation of methane, coal gasification, and water electrolysis.

Depending on the composition of the gaseous $CO_2$-containing substrate, it may also be desirable to treat it to remove any undesired impurities, such as dust particles before introducing it to the fermentation. For example, the gaseous substrate may be filtered or scrubbed using known methods. Further, depending on the composition of the gaseous $CO_2$-containing substrate, the process may include adjusting the $CO_2$-containing substrate to increase or decrease concentrations of $CO_2$ and/or $H_2$ to fall within desired ranges.

Fermentor gas streams: In one aspect, the process includes providing a $CO_2$-containing substrate to a bioreactor where the $CO_2$-containing substrate is a fermentor gas stream. Some examples of fermentor gas streams include fermentor off-gas generated in the fermentation of syngas. Some examples of syngas fermentation are described in U.S. Pat. No. 7,285,402, filed Jul. 23, 2001, which is incorporated herein by reference.

In one aspect, the process has applicability to supporting the production of alcohol from gaseous substrates such as high volume CO-containing industrial gases. In some aspects, a gas that includes CO is derived from carbon containing waste, for example, industrial waste gases or from the gasification of other wastes. The fermentation of CO-containing gas may result in $CO_2$ in fermentor off-gas. As such, the processes represent effective processes for capturing carbon that would otherwise be exhausted into the environment. In this aspect, the off-gas from the fermentation of CO-containing gas may include about 0.5 mole % to about 50 mole % CO.

Blending of gas streams: According to particular aspects, streams from two or more sources can be combined and/or blended to produce a desirable and/or optimized substrate stream. For example, a stream comprising a high concentration of $CO_2$, such as the exhaust from a steel mill, can be combined with a stream comprising high concentrations of $H_2$, such as the off-gas from a steel mill coke oven.

Depending on the composition of the $CO_2$-containing substrate, the $CO_2$-containing substrate may be provided directly to a fermentation process or may be further modified to include an appropriate $H_2$ to $CO_2$ molar ratio. The $CO_2$-containing substrate may include from about 5 to about 90 mole % $CO_2$ and from about 5 to about 90 mole % $H_2$. In one aspect, the $CO_2$ containing gas stream includes about 5 to about 66.6% $CO_2$.

In another aspect, the $CO_2$-containing substrate provided to bioreactor Bx 110 may include from about 0 mole % to about 50 mole % CO, in another aspect, about 0.5 mole % CO to about 50 mole % CO, in another aspect, about 0.5 mole % CO to about 5 mole % CO, and in another aspect, about 2 mole % CO to about 5 mole % CO.

In one aspect, the acetogenic bacteria will have a molar ratio of consumption of $H_2$ to $CO_2$ at a ratio of about 4:1 to about 1:2. Hence, any substrate gas provided to the bioreactor that includes $H_2$ and $CO_2$ can be utilized. However, optimal levels of substrate gas provided to the bioreactor will have a ratio of $H_2$ to $CO_2$ of about 4:1 to about 1:1, in another aspect, about 2:1, and in another aspect, about 3.5:1 to about 1.5:1.

Bioreactor Design and Operation: Descriptions of fermentor designs are described in U.S. Ser. Nos. 13/471,827 and 13/471,858, both filed May 15, 2012, and U.S. Ser. No. 13/473,167, filed May 16, 2012, all of which are incorporated herein by reference.

The fermentation should desirably be carried out under appropriate conditions for the desired fermentation to occur (e.g. $CO_2$-to-acetic acid). Reaction conditions to be considered include pressure, temperature, gas flow rate, liquid flow rate, medium pH, agitation rate (if using a stirred tank reactor), inoculum level, and maximum acetic acid concentration to avoid product inhibition. In this aspect, the process includes reaction conditions in the following ranges:

Pressure: about 0 to about 500 psi, in another aspect about 0 to about 200 psi;
Temperature: about 30° C. to about 42° C.;
Medium pH: about 4 to about 6.9;
Agitation rate: about 100 to about 2000 rpm;
Nutrient supply as described herein.

Acetogenic Bacteria: In one aspect, the microorganisms utilized include anaerobic acetogenic bacteria Mx that include a sodium pump which may also be described as sodium-translocating ATPases (for membrane bioenergetics). Sodium translocating ATPase are described in Muller, "Energy Conservation in Acetogenic Bacteria," Appl. Environ. Microbiol. November 2003, vol. 69, no. 11, pp. 6345-6353, which is incorporated herein by reference. Acetogens that include a sodium-translocating ATPase require about 500 ppm NaCl in their growth medium for growth. To determine if an acetogen includes a sodium-translocating ATPase, the acetogen is inoculated into serum bottles containing about 30 to about 50 ml of growth medium with about 0 to about 2000 ppm NaCl. Normal growth at NaCl concentrations of about 500 ppm or more means that the acetogen includes a sodium-translocating ATPase.

In this aspect, suitable acetogenic bacteria Mx include *Acetobacterium* bacteria, *Acetogenium kivui*, *Acetoanaerobium noterae*, *Acetobacterium woodii*, *Alkalibaculum bacchi* CP11 (ATCC BAA-1772), *Moorella thermoacetica*, *Moorella thermoautotrophica*, *Ruminococcus productus*, *Acetogenium kivui*, and combinations thereof. In another aspect, the microorganism is *Acetobacterium woodii*.

Medium Compositions and Control of Medium Feed Rates: In accordance with one aspect, the fermentation process is started by addition of a suitable medium to the reactor vessel. The liquid contained in the reactor vessel may include any type of suitable nutrient medium or fermentation medium. The nutrient medium will include vitamins and minerals effective for permitting growth of the microorganism being used. Sterilization may not always be required.

Concentrations of various medium components for use in bioreactor Bx 110 with acetogenic bacteria Mx are as follows:

| Element | Concentration mg/L | Feed Rate µg/gram cells/min |
|---|---|---|
| $NH_4^+$ | 82-3280 | 20.5-820 |
| Fe | 0.85-34 | 0.28-8.5 |
| Ni | 0.07-2.81 | 0.023-0.702 |
| Co | 0.037-1.49 | 0.012-0.373 |
| Se | 0.027-1.1 | 0.009-0.274 |
| Zn | 0.59-23.8 | 0.198-5.95 |
| Mo | 0.003-0.397 | 0.003-0.1 |

-continued

| Element | Concentration mg/L | Feed Rate µg/gram cells/min |
|---|---|---|
| chelator | 2.5-100 | 0.83-25 |
| W | 0.8-32.1 | 0.26-8.03 |
| K | 98-3933 | 32.77-983.35 |
| Mg | 0.71-28.69 | 0.23-7.18 |
| Na | 875-35000 | 290-8750 |
| S | 15-625 | 2.08-62.5 |
| P | 20-805 | 6.7-201.3 |
| d-biotin | 0.016-0.64 | 0.005-0.16 |
| thiamine HCl | 0.04-1.6 | 0.01-0.4 |
| calcium-D-pantothenate | 0.02-0.81 | 0.006-0.202 |

Process operation maintains a pH in a range of about 4 to about 6.9, in another aspect, about 5 to about 6.5, in another aspect about 5.1 to about 6, and, in another aspect, about 5.2 to about 6. The medium includes less than about 0.01 g/L yeast extract and less than about 0.01 g/L carbohydrates.

The composition also includes a sodium ion concentration of about 40 to about 500 mmol per liter, in another aspect, about 40 to about 250 mmol per liter and in another aspect, a sodium ion concentration of about 50 to about 200 mmol per liter. In one aspect, the sodium ion concentration is about 500 ppm to about 8000 ppm, in another aspect, about 1000 ppm to about 7000 ppm, in another aspect, about 3000 ppm to about 6000 ppm, in another aspect, about 2000 to about 5000 ppm Na, and in another aspect, about 3000 to about 4000 ppm Na. The sodium ion source is provided by a compound selected from the group consisting of sodium chloride, sodium hydroxide, sodium phosphate, sodium sulfate, sodium nitrate, sodium bicarbonate, sodium bisulfate and mixtures thereof.

The composition includes a source of molybdenum. In this aspect the molybdenum concentration is about 3.97 µg/L to about 396.5 µg/L, and in another aspect, about 7.93 µg/L to about 198.25 µg/L. Sources of molybdenum include $Na_2MoO_4$, $CaMoO_4$, $FeMoO_4$ and mixtures thereof.

The composition may also include a complexing agent. In this aspect, a complexing agent may be included in the composition when the composition has a pH of about 5.2 or greater. The complexing agent may include ethylenediaminetetraacetic acid (EDTA), ethylenediamine diacetic acid (EDDA), ethylenediamine disuccinic acid (EDDS) and mixtures thereof.

The composition may include one or more of a source of $NH_4^+$, P, K, Fe, Ni, Co, Se, Zn, or Mg. Sources of each of these elements may be as follows.

$NH_4^+$: The nitrogen may be provided from a nitrogen source selected from the group consisting of ammonium hydroxide, ammonium chloride, ammonium phosphate, ammonium sulfate, ammonium nitrate, and mixtures thereof.

P: The phosphorous may be provided from a phosphorous source selected from the group consisting of phosphoric acid, ammonium phosphate, potassium phosphate, and mixtures thereof.

K: The potassium may be, provided from a potassium source selected from the group consisting of potassium chloride, potassium phosphate, potassium nitrate, potassium sulfate, and mixtures thereof.

Fe: The iron may be provided from an iron source selected from the group consisting of ferrous chloride, ferrous sulfate, and mixtures thereof.

Ni: The nickel may be provided from a nickel source selected from the group consisting of nickel chloride, nickel sulfate, nickel nitrate, and mixtures thereof.

Co: The cobalt may be provided from a cobalt source selected from the group consisting of cobalt chloride, cobalt fluoride, cobalt bromide, cobalt iodide, and mixtures thereof.

Se: The selenium may be provided from $Na_2SeO_3$, $C_3H_6NO_2Se$, and mixtures thereof.

Zn: The zinc may be provided from $ZnSO_4$.

W: The tungsten may be provided from a tungsten source selected from the group consisting of sodium tungstate, calcium tungstate, potassium tungstate, and mixtures thereof.

Mg: The magnesium may be provided from a magnesium source selected from the group consisting of magnesium chloride, magnesium sulfate, magnesium phosphate, and mixtures thereof.

S: The composition may also include sulfur. The sulfur may be provided from a sulfur source selected from the group consisting of cysteine, sodium sulfide, NaHS, $NaH_2S$ and mixtures thereof.

Startup: Upon inoculation, an initial feed gas supply rate is established effective for supplying the initial population of microorganisms. Effluent gas is analyzed to determine the content of the effluent gas. Results of gas analysis are used to control feed gas rates. In this aspect, the process provides a minimal cell density of about 0.1 grams per liter. In another aspect, the process provides a calculated $CO_2$ quantities per unit time (mmol/min) to initial cell density (grams/liter) ratio of about 0.05 to about 1, and in another aspect, about 0.01 to about 4.

In one aspect, nutrients may be added to the culture to increase cell growth rates. Suitable nutrients may include non-carbohydrate fractions of yeast extract.

Post-startup: Upon reaching desired levels, liquid phase and cellular material is withdrawn from the reactor and replenished with medium. The fermentation process is effective for increasing cell density as compared to a starting cell density. In this aspect, the process provides an average cell density of about 2 to about 50 grams/liter, in another aspect, about 2 to about 30 grams/liter, in another aspect, about 2 to about 20 grams/liter, in another aspect, about 2 to about 10 grams/liter, in another aspect, about 5 to about 10 grams/liter, and in another aspect, about 2 to about 6 grams/liter.

Production of Organic Acid: In another aspect, the process provides a source of C1 to C10 organic acids. In this aspect, the process may include obtaining acid product or products from the fermentation liquid broth. In this aspect, provides a specific organic acid productivity of about 0.2 to about 50 grams organic acid/liter/day/g cells, in another aspect, about 0.2 to about 20 grams organic acid/liter/day/g cells, in another aspect, about 10 to about 50 grams organic acid/liter/day/g cells, in another aspect, about 14 to about 30 grams organic acid/liter/day/g cells, in another aspect, about 2 to about 20 grams organic acid/liter/day/g cells and in another aspect, about 15 to about 25 grams organic acid/liter/day/g cells. In one aspect, the organic acid is acetic acid or butyric acid, or a mixture of both.

Conversions of $CO_2$ and $H_2$: The process is effective for providing a $CO_2$ uptake of about 0.05 to about 1.5 mmol $CO_2$/minute/gram dry cells, an $H_2$ uptake of about 0.08 to about 1.5 mmol $H_2$/minute/gram dry cells. The process is effective for providing about 25 to about 100% conversion of $CO_2$, in another aspect, about 50 to about 100% conversion of $CO_2$, and in another aspect, about 75 to about 100% conversion of $CO_2$. In another aspect, the process is effective for providing about 25 to about 100% conversion of $H_2$, in another aspect, about 50 to about 100% conversion of $H_2$, and in another aspect, about 75 to about 100% conversion of $H_2$.

Figure 4:
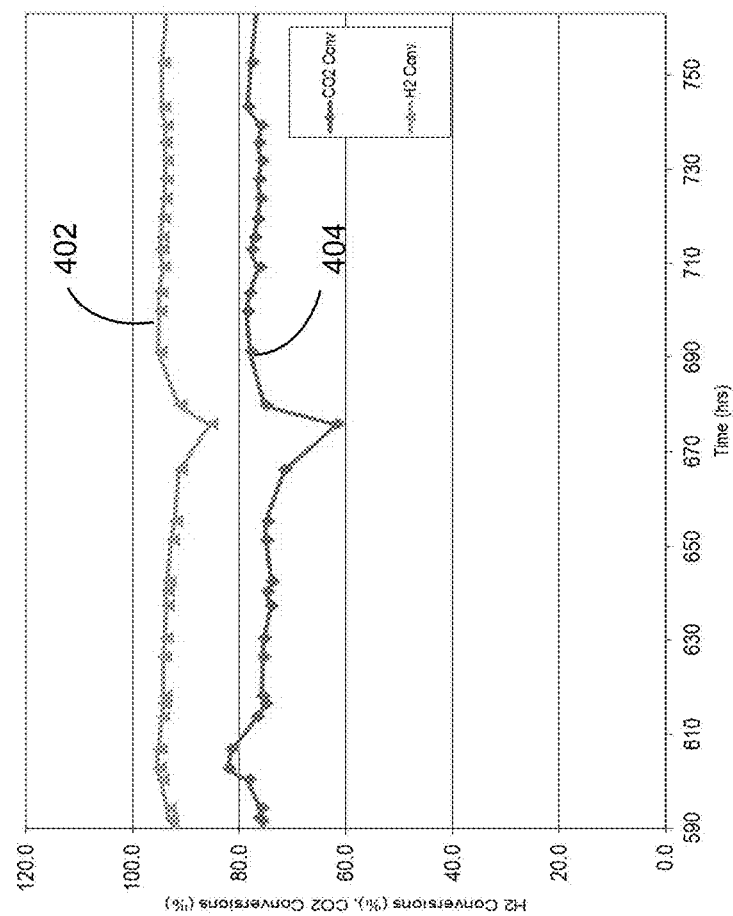
FIG. 4 shows a graph of $CO_2$ conversion and $H_2$ conversion by *Acetobacterium woodii* in a bioreactor.
Figure 5:
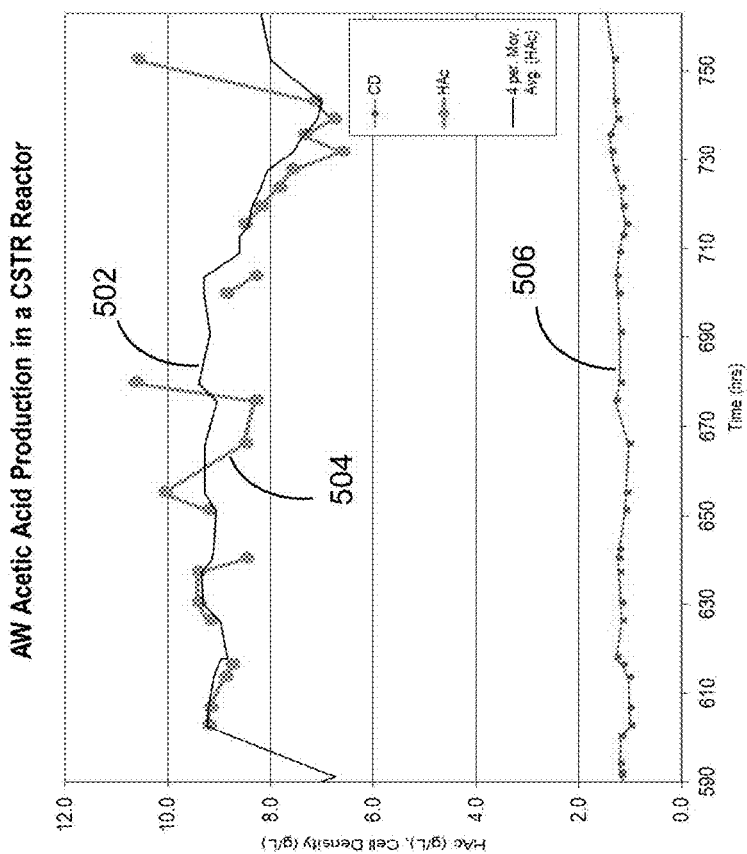
FIG. 5 illustrates acetic acid production by *Acetobacterium woodii*.

FIG. 4 shows a graph of $CO_2$ conversion 404 and $H_2$ conversion 402 by *Acetobacterium woodii*. A graphical illustration of acetic acid production 504 and its moving average 502, and cell density 506 versus time is shown in FIG. 5.

EXAMPLES

Example 1: Preparation of *Acetobacterium woodii*

An initial lyophilized pellet of *Acetobacterium woodii* was obtained from German culture collection DSMZ, strain ID DSM-1030. Culture was initially revived from lyophilized pellet using rich medium (fructose and yeast extract). An adaptation method was used to remove fructose from serum bottle medium where concentration of fructose in growth medium was stepped down 75%, 50%, 10%. Growth rate and gas usage was used as an indicator of adaptation. (approximately 5 weeks). Preliminary pH adaptation work in serum bottles reduced required pH from 7.4 to 6.0 (3 weeks). At this point, culture was amplified and inoculated into a reactor. In a reactor culture was further adapted to grow in lower pH of 5.2 to 5.7.

Example 2: CSTR Reactor Startup Method for *Acetobacterium woodii*

A synthesis gas containing $CO_2$ and $H_2$ was continuously introduced into a stirred tank bioreactor containing *Acetobacterium woodii*, along with a liquid medium containing vitamins, trace metals, cysteine (as sulfur source), and salts as described herein.

A New Brunswick Bioflow 310 reactor containing the fermentation medium was started, with actively growing *Acetobacterium woodii*. The rate of agitation of the reactor was set to 200 rpm. This agitation rate was increased throughout the experiment from 200 to 600 rpm. Feed gas flow to the reactor was increased from an initial at 49 mL/min to 137 mL/min. Temperature in the bioreactor was maintained at 33.5° C. throughout the experiment. Samples of gas feed into the bioreactor and off-gas from the bioreactor and fermentation broth in the bioreactor were taken at intervals, for example feed gas, off-gas and fermentation broth were sampled about daily, once two hours and once four hours respectively. Above samples were analyzed for consumption or production of various gas components, broth acetic acid concentration, and the optical density (cell density) of the culture. The unaroused volume of the reactor was maintained between 1600 to 1750 ml throughout the experiment. Also, the gas flow to the reactor was maintained at required gas flow rates by using a mass flow controller. The feed syngas composition was 70% $H_2$, 25% $CO_2$ and 5% $N_2$. This experiment was concluded when stable operation was reached.

A cell recycle system (CRS) was attached to the reactor before the start of the experiment. During the experiment, the rate of flow of nutrients (growth medium) to the reactor was as indicated in the Table. Medium feed rate was maintained throughout the experiment. The base (0.5M NaOH) feed rate for pH control was 0.14-0.44 ml/min, and through the CRS, 5.1-5.4 ml/min permeate was drawn out from the reactor.

$H_2$ and $CO_2$ in the feed gas was fixed into cell material and acetic acid. The removal of $H_2$, and $CO_2$ was calculated by comparing inlet gas composition with the effluent gas composition. Component gas uptake is expressed in % of gas molecules converted by bacteria. In this experiment the following conversions were achieved; $H_2$: 40%-54%, $CO_2$: 28%-70%. In this experiment the rate of acetic acid production was 5-23 g/l/day.

Results can be summarized as follows:

| | |
|---|---|
| Specific CO2 uptake (mmol $CO_2$/min/gram dry cells) | 0.17-0.33 |
| Specific H2 uptake (mmol $H_2$/min/gram dry cells) | 0.20-0.9 |
| Acetic Acid productivity (g/L/day) | 5-23 |
| Specific Acetic Acid productivity (g/L/day/gCells) | 4.6-11.6 |
| Average Cell Density (g/L) | 1.5 |

Example 3: Fermentation of $CO_2$, CO and $H_2$ by *Acetobacterium woodii*

A gas containing $CO_2$ and $H_2$ was continuously introduced into a stirred tank bioreactor containing *Acetobacterium woodii*, along with a conventional liquid medium containing vitamins, trace metals, and salts. Fermentations were started as described in Example 2 and then continued to stable operation. In this Example, the feed gas included 5 mole % CO.

Figure 6:
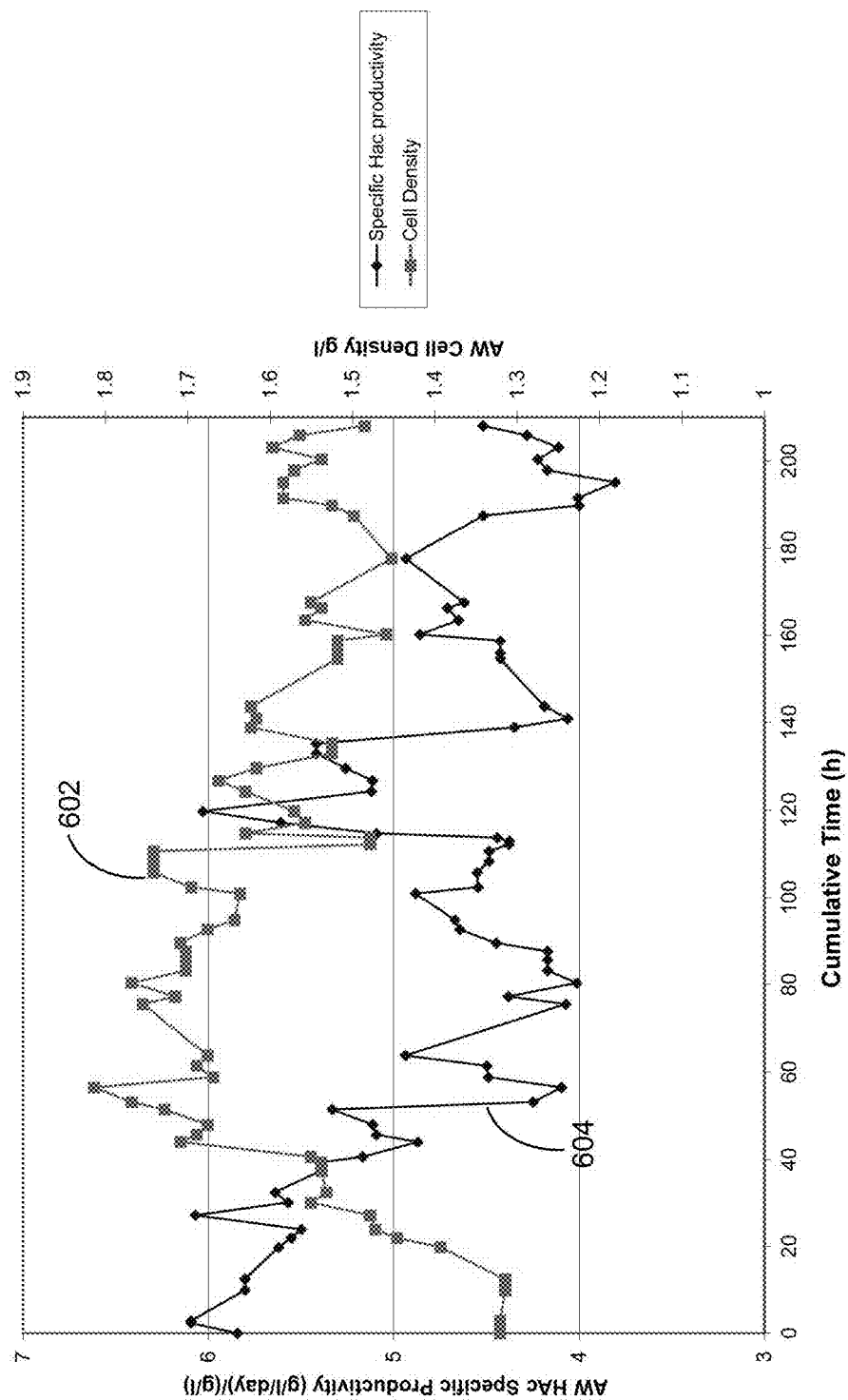
FIG. 6 shows specific acetic acid productivity.
Figure 7:
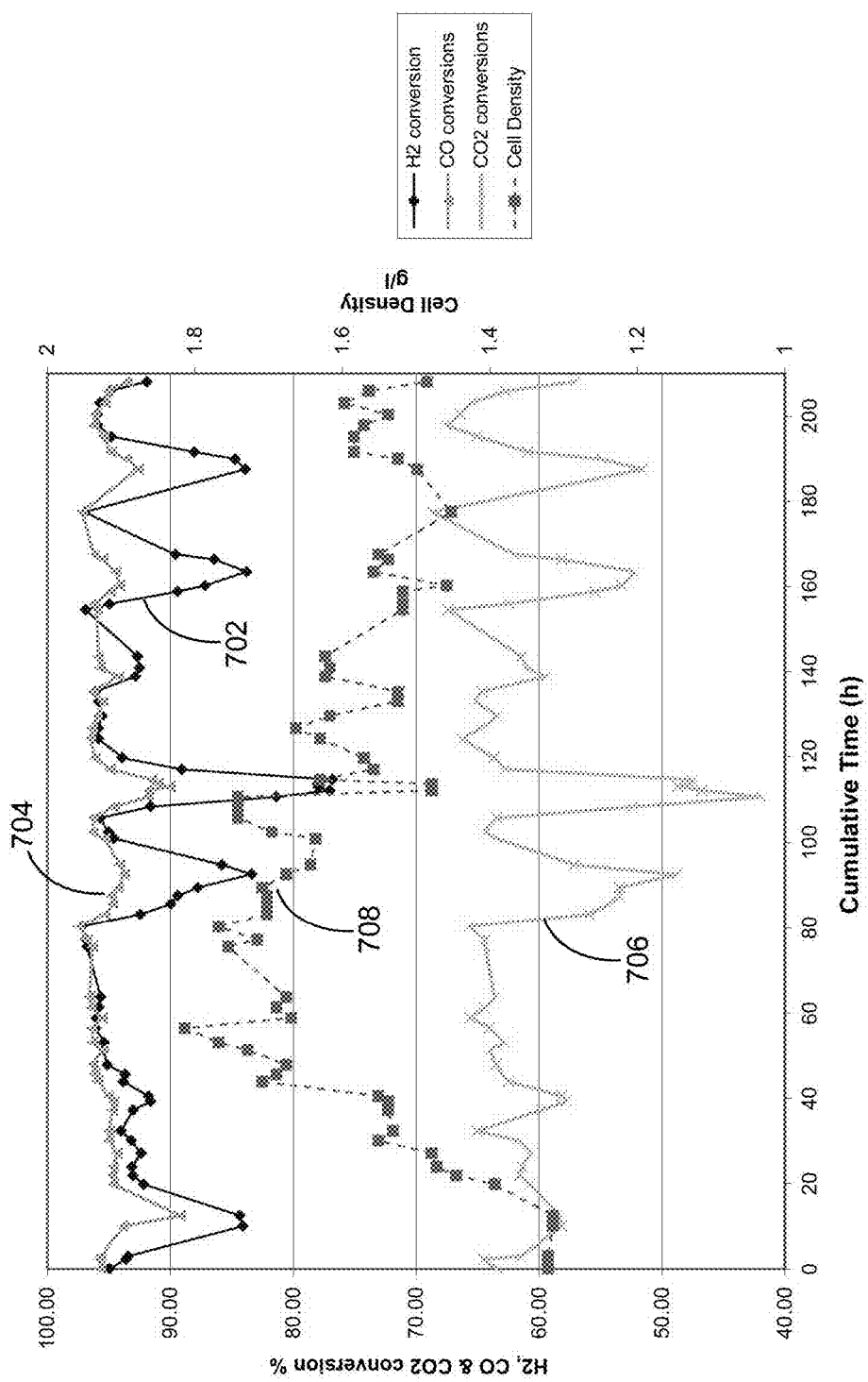
FIG. 7 shows utilization of CO, $CO_2$ and $H_2$ by *Acetobacterium woodii*.

FIG. 6 and FIG. 7 describe growth of *Acetobacterium woodii* in the presence of 5% CO. FIG. 6 illustrates cell density 602 and specific acetic acid productivity 604 versus time. FIG. 7 illustrates $H_2$ conversion 702, CO conversions 704, $CO_2$ conversions 706, and cell density 708.

Example 4: Growth and Maintenance of *Acetobacterium woodii* Culture at pH 5.2 without a Chelating Agent (EDTA) in the Growth Medium A gas stream containing $CO_2$ and $H_2$ was continuously introduced into a stirred tank bioreactor containing *Acetobacterium Woodii* along with a growth medium as described herein.

A New Brunswick Bioflow 115 reactor containing fermentation medium was started with actively growing *Acetobacterium woodii* (AW). The rate of agitation of the reactor was set to 600 rpm. This agitation rate remained constant throughout the experiment. Feed gas flow to the reactor was maintained at 36.6 mL/min to 44.4 mL/min. Temperature in the bioreactor was maintained at 33° C. throughout the experiment. Na+ levels were kept at 3500 to 4000 ppm. Samples of gas feed into the bioreactor and off-gas from the bioreactor and fermentation broth in the bioreactor were taken at intervals, for example feed gas, offs-gas and fermentation broth was sampled about daily, once two hours and once four hours respectively. Above samples were analyzed for consumption or production of various gas components, broth, acetic acid concentration, and the optical density (cell density) of the culture. The unaroused volume of the reactor was maintained between 1900 to 2275 ml throughout the experiment. Also, the gas flow to the reactor was maintained at required gas flow rates using a mass flow controller. The feed syngas composition of this experiment was 70% $H_2$, 25% $CO_2$ and 5% $N_2$.

A cell recycle system (CRS) was attached to the reactor before the start of the experiment During the experiment, the rate of flow of nutrients (growth medium) to the reactor was maintained at 2.8 ml/min. Medium feed rate was maintained throughout the experiment. The average rate of base (NaOH) requirement to maintain pH at 5.2 was 0.075 ml/min, and through the CRS, 2.9 ml/min permeate was drawn out from the reactor.

H$_2$ and CO$_2$ in the feed gas was fixed into cell material and acetic acid. The removal of H$_2$ and CO$_2$ was calculated by comparing inlet gas composition with the effluent gas composition. Component gas uptake can be expressed in % of gas molecules converted by bacteria.

Figure 8:
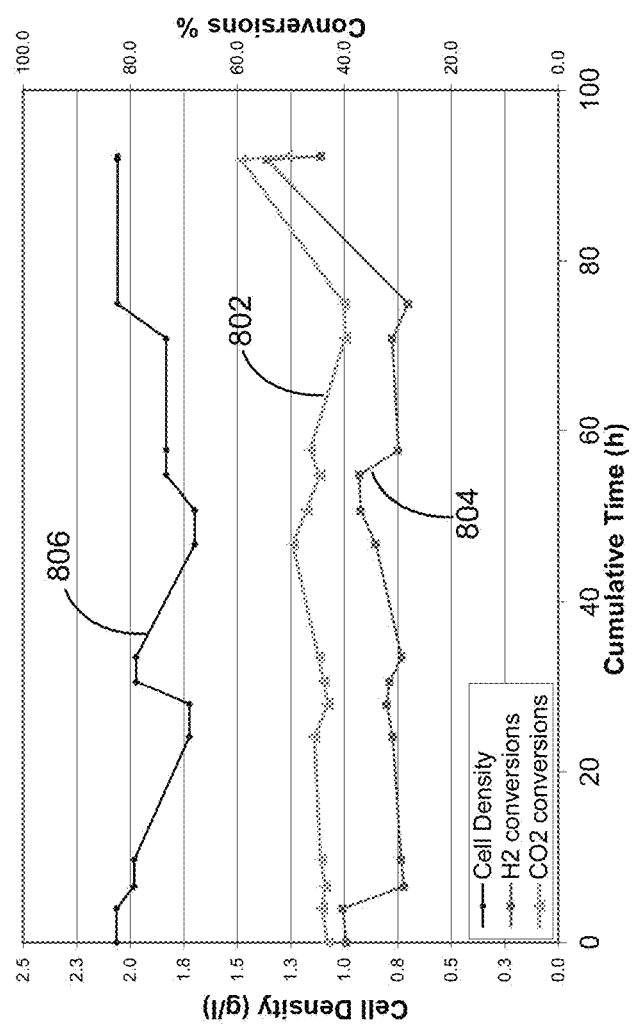
FIG. 8 illustrates $CO_2$ conversions, $H_2$ conversions and cell density of *Acetobacterium woodii* at pH 5.2 without a chelating agent in the growth medium.

The following conversions were achieved:
H$_2$: 28% to 54%
CO$_2$: 40% to 59%
The rate of acetic acid production was 0.7949 (g/L/day)
Average cell density of the culture was 1.9 g/L
CO$_2$ conversions 802, H$_2$ conversions 804 and cell density 806 are shown in FIG. 8.

Example 5: Use of EDDA in Growth Medium

Figure 9:
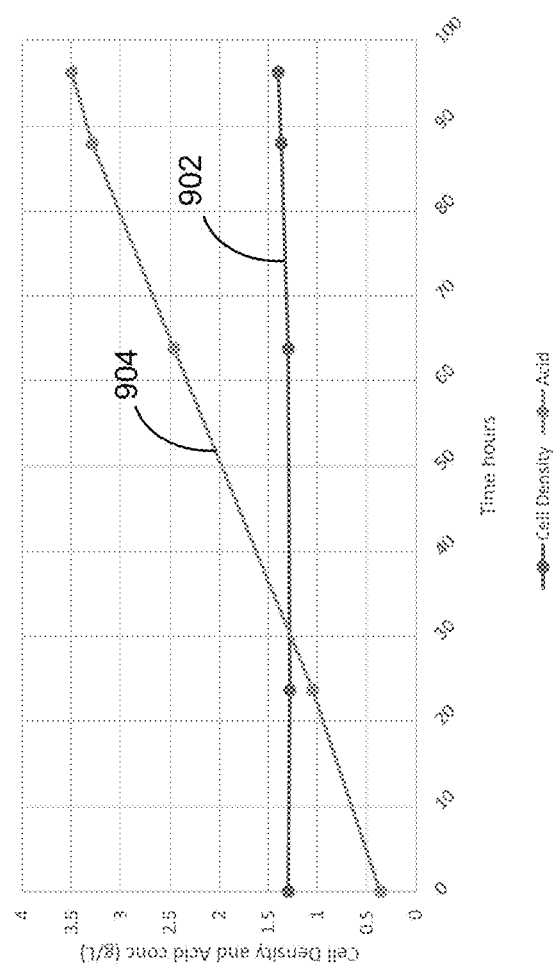
FIG. 9 describes growth of *Acetobacterium woodii* using ethylenediamine diacetic acid (EDDA) as a chelating (complexing) agent in the growth medium.

Fermentations were started as described in Example 2 and included the use of ethylenediamine diacetic acid (EDDA) as a chelating (complexing) agent. Chelating agents are employed to keep metals in solution as the solubility of some of the metals employed in AW indium decreases with the increasing pH. If the pH of the reactor broth is above pH 5.2, chelating agents are employed to provide sufficient amounts of nutrients to A. FIG. 9 shows a representative 96 hr period of the experiment that illustrates the ability to maintain cell density 902 while producing increasing concentrations of acetic acid 904.

Example 6: Effect of Molybdenum Removal and Re-Addition on Cell Metabolism

Fermentations were started as described in Example 2 and then continued to stable operation. Molybdenum was removed from culture media and then re-added to the growth medium after acetic acid productivity had dropped to 75% of its starting concentration.

Figure 10:
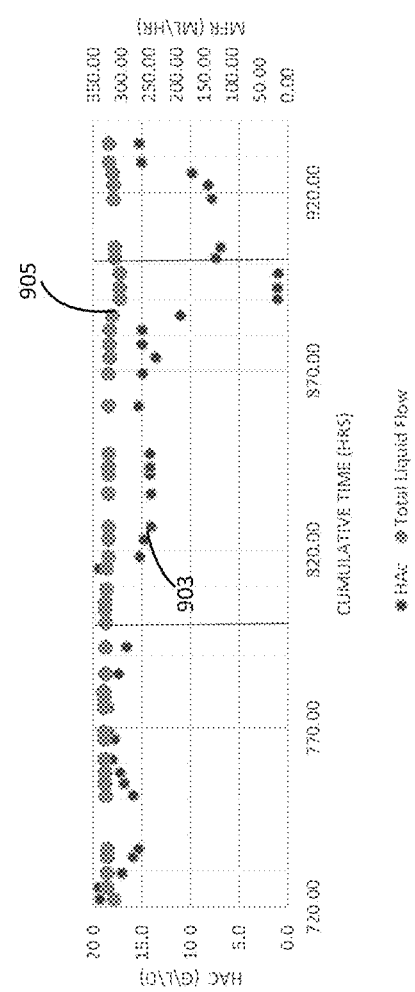
FIG. 10 illustrates the effect of molybdenum on acetic acid production by *Acetobacterium woodii*.

FIG. 10 illustrates acetic acid productivity 903 plotted against its media flow rate 905 with the red lines indicating the removal and re-addition of molybdenum to the growth medium. Starting at about 810 cumulative hours, a downward trend of HAc was observed with the molybdenum removal occurring at about 795 cumulative hours. This downward trend decreased, plateaued and then was reversed into an upward trend in correspondence with the re-addition of molybdenum to the media at about 900 hours.

Figure 11:
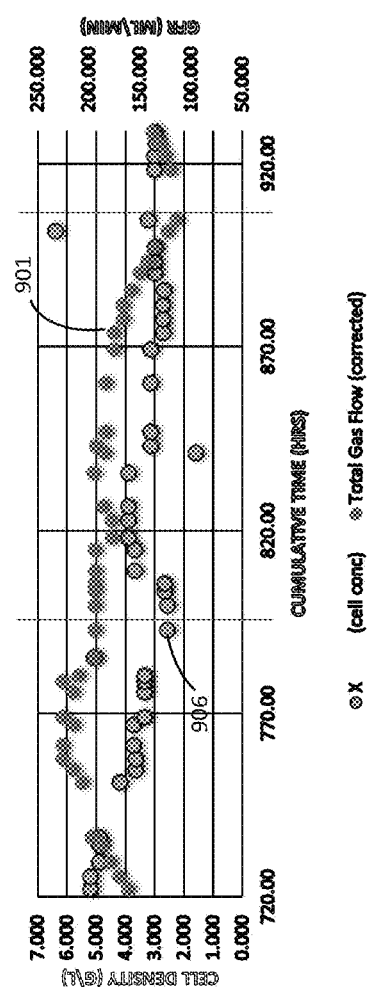
FIG. 11 illustrates the effect of molybdenum on required gas flow rate and cell density of *Acetobacterium woodii*.

FIG. 11 illustrates cell density 906 and gas flow rate (GFR) 901 plotted against time with the red lines indicating the removal and re-addition of molybdenum to the growth medium. Starting at about 840 cumulative hours, the required GFR was less compared to before the molybdenum removal occurring at about 795 cumulative hours. This downward trend was reversed into an upward trend in correspondence with the return of molybdenum to the media at about 900 hours. Required gas flow rate was determined by the CO$_2$ and H$_2$ conversions of the culture.

Example 7: A Continuous Process for Conversion of CO with *Clostridium ljungdahlii*

Synthesis or waste gas containing CO and/or CO$_2$/H$_2$ was continuously introduced into a stirred tank bioreactor containing a strain of *Clostridium ljungdahlii*, along with a fermentation medium containing vitamins, trace metals and salts as described herein.

New Brunswick BioFlow 310 reactor containing a suitable medium was inoculated with 0.38 g/l of actively growing *Clostridium ljungdahlii*. Before inoculation, the rate of agitation of the reactor was set to 800 rpm, gas flow to the reactor was adjusted to 20 ml/min and a cell recycle system was attached to the reactor. Gas and liquid samples taken from the reactor at every 1 to 4-hour intervals were analyzed for consumption or production of various gas components, broth acetic acid concentration, broth ethanol concentration and the optical density of the culture. Also, the composition, of the feed-gas was measured daily and the flow to the reactor was maintained at required gas flow rates by using a mass flow controller. Once H$_2$ conversion reached 32% media flow to the reactor was started at 1 ml/min and drawn a permeate of 0.95 ml/min. Syngas flow to the reactor was increased based on H$_2$ conversion of the culture: gas flow was increased by 10% if H$_2$ conversion is 32% or above. Cell mass increased with time and reached 3 g/l of cell mass within 72 hours after the inoculation of the reactor. At this point culture was producing more than 18 g/l of ethanol. A liquid chromatograph was used to measure the broth ethanol and acetic acid concentrations. A gas chromatograph was used to measure the components of the syngas. Neutralizing agent such as NH4OH was used to maintain pH of the culture around 4.5. Cell density of the reactor was maintained around 3 g/L by adjusting the rate of permeate draw. Reactor was set up such that the rate of permeate draw inversely control the rate of cell purge from the reactor. Operating pressure was atmospheric.

As bacterial fermentation proceeds over a period of several hours post-inoculation, CO$_2$ is produced from the conversion of CO, and H$_2$ is consumed along with the CO. The production method and bacterial fermentation reactor system are then maintained at a steady state producing 15 to 35 g/L ethanol and 0 to 5 g/L acetate as products, with only occasional small adjustments to maintain acetic acid concentration in the above range and cell density at around 3 g/L This method of continuous fermentation allows for the continuous production and maintenance of high ethanol concentrations with low by-product acetate concentrations under stable operating conditions to enhance use of subject bacterial on an industrial scale for ethanol production.

Example 8: Effect of Acetic Acid Addition to *Clostridium ljungdahlii*

Fermentations with *Clostridium ljungdahlii* were conducted as describe in Example 7.

Each trial was conducted for 72 hours in the presence of 5 g/L NaCl and the following amounts of acetic acid in the reactor broth.
Control—no additions.
Trial 1—2 g/L acetic acid
Trial 2—4 g/L acetic acid
Trial 3—6 g/L acetic acid Addition of acetic acid to the medium had an effect on the specific productivity of ethanol. As concentrations of acetic acid increased, ethanol production also increased accordingly. There was no noticeable change in acetic acid productivity, regardless of concentration in the medium. All exogenously added acid appeared to be converted by the culture to ethanol. There was a significant increase in specific CO uptake in cultures that had exogenously added acid in the medium when compared to the control, with the highest concentration reaching the highest level of uptake at about 0.750 mmol/min/g of cells. The control averaged about 0.500 mmol/min/g of cells during this time. Acetic acid concentration also increased the hydrogen uptake. Specific productivity at steady state (g/L/day/g of cells) was as follows.

|         | EtOH |         | Acetic Acid |         |
| ------- | ---- | ------- | ----------- | ------- |
|         | Avg  | Std Dev | Avg         | Std Dev |
| Control | 6.24 | 1.33    | 1.20        | 0.39    |
| 2 g/L HAc | 6.33 | 1.48  | 1.07        | 0.34    |
| 4 g/L HAc | 7.42 | 1.82  | 1.16        | 0.20    |
| 6 g/L HAc | 8.50 | 0.35  | 1.51        | 0.20    |

Figure 12:
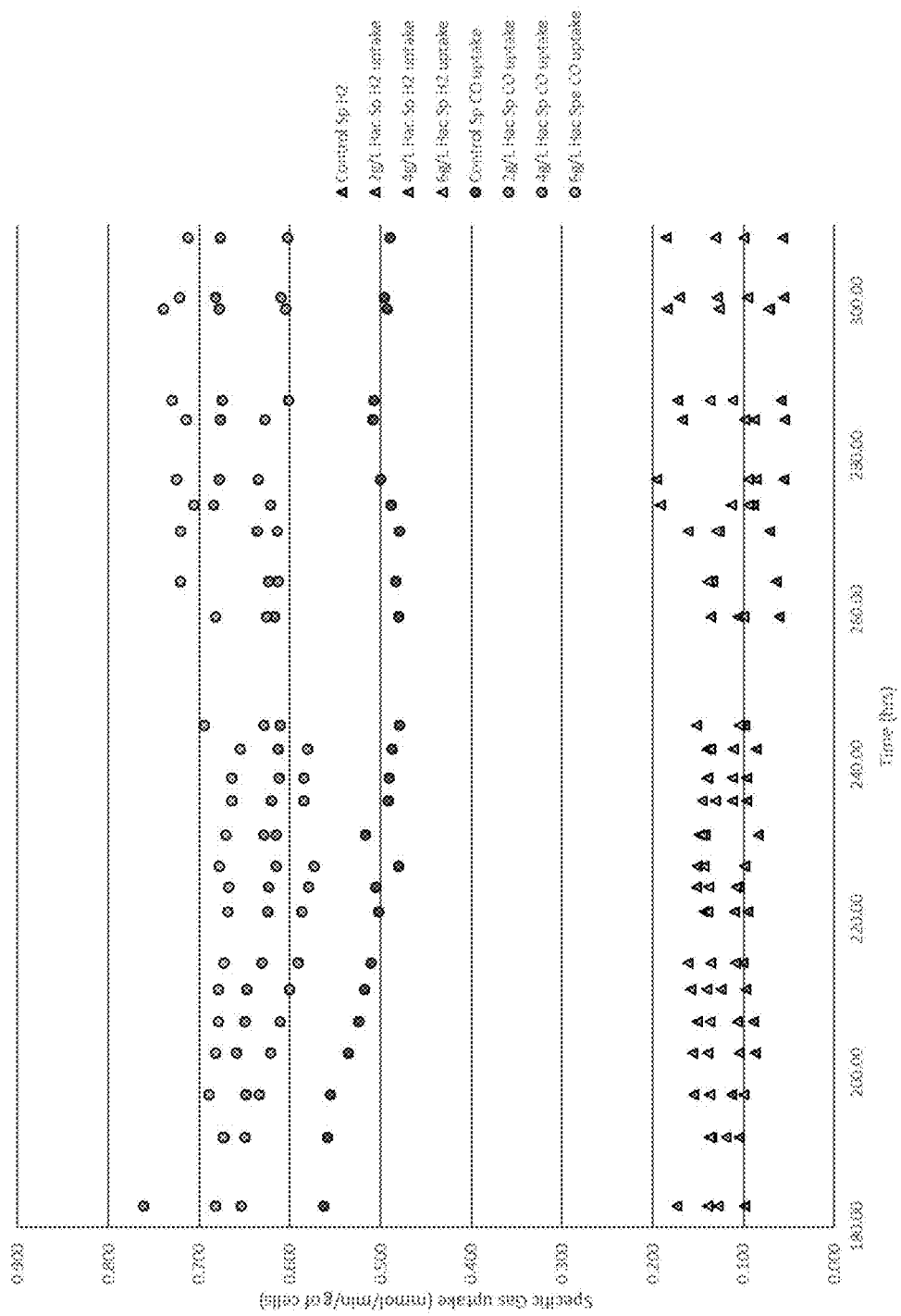
FIG. 12 illustrates specific gas uptake by *Clostridium ljungdahlii* with various concentrations of acetic acid.

FIG. 12 illustrates specific gas uptake by *Clostridium ljungdahlii* with various concentrations of acetic acid.

Example 9: Two-Stage Reactor Using *Clostridium ljungdahlii* and *Acetobacterium woodii*

A two-stage reactor was configured as shown in FIG. 1. The two-stage reactor included a stirred tank bioreactor Bi 120 and stirred tank bioreactor Bx 110. Each reactor contained a liquid medium containing vitamins, trace metals, cysteine (as sulfur source), and salts as described herein. Bioreactor Bi 120 was started with actively growing *Clostridium ljungdahlii* and Bioreactor Bx 110 was started with actively growing *Acetobacterium woodii*.

In bioreactor Bx 110, 0.5 M NaOH is being used as an agent to keep the pH around 6.0. The approximate usage of NaOH per gram of cells per hour is 0.21.

A gaseous substrate Gi 186 containing 55% $H_2$, 12% $N_2$, 33% CO was introduced into bioreactor Bi 120. A gaseous exit stream (Gp) from bioreactor Bi 120 was provided to bioreactor Bx 110 via gas stream connection 184.

Water in the system was in a "closed" configuration and passed from bioreactor 120 to distillation 188 via permeate/ethanol conduit 192. Water (distillation bottoms) was returned to bioreactor Bx 110 via water recycle line 202. Acetic acid from bioreactor Bx 110 was sent to bioreactor Bi 120 via permeate acetic acid line 182.

The fermentation was conducted for approximately 120 hours starting from water loop closure. The system was equilibrated over the first 58 hours and data collected over final 62 hrs. Influent gas streams, 186 (Gi) and 187 (Gx), and effluent gas streams 184 (Gp) and 207 (bioreactor Bx 110 off-gas stream) of both reactors were analyzed roughly every four hours. Analysis was performed using gas chromatography. Data was expressed as % composition. Product analysis of ethanol, acetic acid, and butanol was preformed using liquid chromatography (LC) roughly every four hours. Cell concentration of both reactors was monitored roughly every 4 hours.

Average % composition and gas flow rates were as follows:

|  | $H_2$ | $N_2$ | CO | $CO_2$ | GFR (ml/min) |
| --- | --- | --- | --- | --- | --- |
| Gaseous Substrate Gi (Influent gas streams to bioreactor 120) | 54.8 | 11.3 | 32.29 | N/A | 569 |
| Gaseous Substrate Gp (effluent gas streams to bioreactor 120) | 58.6 | 13.0 | 3.85 | 22.4 | 439 |
| Gaseous Substrate Gp (Influent gas streams to bioreactor 110) | 58.6 | 13.0 | 3.85 | 22.4 | 224 |
| Gaseous Substrate Vent (effluent gas streams to bioreactor 110) | 41.7 | 48.1 | 0.7 | 3.8 | 132 |

Gaseous influent feed rate into bioreactor Bi 120 and Bx 110 were maintained using mass flow controllers (MFC). Effluent gas flow rates of bioreactor Bx 110 and Bi 120 were measured using a burette. The gas flow rate to bioreactor Bx 110 was calculated using the ratio of $N_2$ composition of influent and effluent gas streams of bioreactor Bx 110.

In this experiment only a fraction of gas leaving bioreactor Bi 120 was feed to bioreactor Bx 110. In one instance 51% of effluent gas from bioreactor Bi 120 was fed to bioreactor Bx 110. In another instance 60% of effluent gas from bioreactor Bi 120 was fed to bioreactor Bx 110. Ethanol productivity was as follows.

| Reactor | Ethanol (g/L/g *Clostridium* cells/day) |
| --- | --- |
| Bioreactor 120 (*Clostridium ljungdahlii*) | 7.4 |
| When 51% effluent gas of 120 fed to 110 Bioreactor 120 (*Clostridium ljungdahlii*) + Bioreactor 110 (*Acetobacterium woodii*) | 14.3 |
| When 60% effluent gas of 120 fed to 110 Bioreactor 120 (*Clostridium ljungdahlii*) + Bioreactor 110 (*Acetobacterium woodii*) | 16.2 |

Specific ethanol productivity values for two reactor system was calculated using productivity of bioreactor Bi 120. *Acetobacterium woodii* produced zero to negligible amounts of ethanol in these experiments. *Clostridium ljungdahlii* specific ethanol productivity (when not combined with bioreactor 110) used in this table was measured before the two reactors were connected. If 100% of off gas from bioreactor Bi 120 is supplied, to bioreactor Bx 110, it is projected that specific ethanol productivity is 24.4 g/L/g *Clostridium* cells/day.

Average carbon capture of the system was as follows.

| Reactor | % CO conversion | % CO2 conversion | % carbon conversion | % H2 conversion |
| --- | --- | --- | --- | --- |
| Bioreactor 120 (*Clostridium ljungdahlii*) | 90 | N/A | 35 | 18 |
| Bioreactor 110 (*Acetobacterium woodii*) | 95 | 96 | 96 | 81 |
| Bioreactor 120 (*Clostridium ljungdahlii*) + Bioreactor 110 (*Acetobacterium woodii*) | 99.5 | 96 | 97.5 | 83.7 |

$CO_2$ is produced in bioreactor 120 through the water-gas shift reaction.

Figure 13:
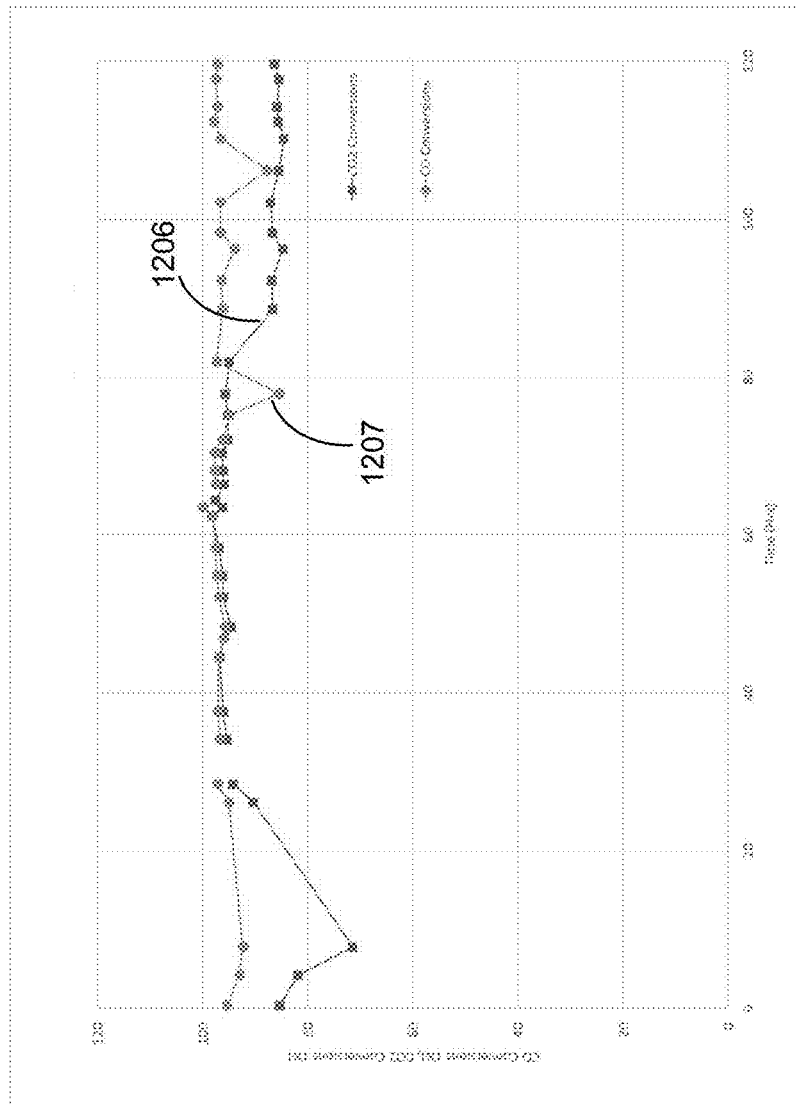
FIG. 13 shows CO and $CO_2$ usage in a two-stage bioreactor system with *Clostridium ljungdahlii* and *Acetobacterium woodii*.

FIG. 13 shows CO 1207 and $CO_2$ 1206 usage in bioreactor 110 when coupled with bioreactor 120. Conversions are calculated using molar % of effluent gas/influent gas.

Example 10: Two-Stage Reactor Using *Clostridium ljungdahlii* and *Acetobacterium*

A two-stage reactor was configured as shown in FIG. 1. The two-stage reactor included a stirred tank bioreactor 120 (Bi) and stirred tank bioreactor 110 (Bx). Each reactor contained a liquid medium containing vitamins, trace metals, cysteine (as sulfur source), and salts as described herein. Bioreactor 120 (Bi) was started with actively growing of *Clostridium ljungdahlii* and Bioreactor 110 (Bx) was started with actively growing *Acetobacterium woodii*.

In bioreactor Bx 110, 0.5 M NaOH is being used as an agent to keep the pH around 5.55. The approximate usage of NaOH per grain of cells per hour was 0.13 ml/min.

A gaseous substrate 186 (Gi) containing 56% $H_2$, 11% $CH_4$, 33% CO was introduced into bioreactor Bi 120. A gaseous exit stream (Gp) from bioreactor 120 was provided to bioreactor Bx 110 via gas stream connection 184.

Water in the system was in a "closed" configuration and passed from bioreactor Bi 120 to distillation 188 via permeate/ethanol conduit 192. Water (distillation bottoms) was returned to bioreactor Bx 110 via water recycle line 202. Acetic acid from, bioreactor Bx 110 was sent to bioreactor Bi 120 via permeate acetic acid line 182.

The fermentation was conducted for approximately 96 hours starting from water loop closure. The system was equilibrated over the first 48 hours and data collected over the final 48 hrs. Influent gas streams, 186 (Gi) and 187 (Gx), and effluent gas streams 184 (Gp) and 207 (vent stream) of both, reactors were analyzed roughly every four hours. Analysis was performed using gas chromatography. Data was expressed as % composition. Product analysis of ethanol, acetic acid, and butanol was preformed using GC roughly every four hours. Cell concentration of both reactors was monitored roughly every 4 hours.

Average % composition and gas flow rates were as follows:

|  | $H_2$ | $CH_4$ | CO | $CO_2$ | GFR (ml/min) |
|---|---|---|---|---|---|
| Gaseous Substrate Gi (Influent gas stream of bioreactor 120) | 56 | 11 | 33 | N/A | 415 |
| Gaseous Substrate Gp (Effluent gas stream of bioreactor 120) | 61.4 | 13.4 | 4.2 | 21.9 | 342 |
| Gaseous Substrate Gp (Influent gas stream of bioreactor 110) | 62 | 13.6 | 4.2 | 22.1 | 98 |
| bioreactor 110 off gas (Effluent gas stream of bioreactor 110) | 42.2 | 45.6 | 0.2 | 13.9 | 23 |

Gaseous influent feed rate into bioreactor Bi 120 and Bx 110 were maintained using mass flow controllers (MFC). Effluent gas flow rates of bioreactor Bx 110 and Bi 120 were measured using a burette. The gas flow rate to the bioreactor Bx 110 was calculated using the ratio of $CH_4$ composition of influent and effluent gas streams of bioreactor Bx 110.

In this experiment only a fraction of gas leaving bioreactor Bi 120 was fed to the bioreactor Bx 110. Gas feed to the bioreactor Bx 110 was 22.5% of total off gas from bioreactor Bi 120.

Ethanol productivity was as follows.

| Reactor | Ethanol (g/L/g *Clostridium* cells/day) |
|---|---|
| Bioreactor 120 (*Clostridium ljungdahlii*) | 5.5 |
| Bioreactor 120 (*Clostridium ljungdahlii*) + Bioreactor 110 (*Acetobacterium woodii*) | 8.2 |

Specific ethanol productivity values for two reactor system was calculated using productivity of bioreactor Bi 120. *Acetobacterium woodii* produced zero to negligible amounts of ethanol in these experiments. *Clostridium ljungdahlii* specific productivity (when not combined with bioreactor Bx 110) shown in this table was measured before the two reactors are connected. If 100% of off gas from bioreactor Bi 120 is supplied to the bioreactor Bx 110, it is projected that specific ethanol productivity of the system is 36.4 g/L/g *Clostridium* cells/day.

Butanol productivity was as follows.

| Reactor | Butanol (g/L/g *Clostridium* cells/day) |
|---|---|
| Bioreactor 120 (*Clostridium ljungdahlii*) | N/A |
| Bioreactor 120 (*Clostridium ljungdahlii*) + Bioreactor 110 (*Acetobacterium woodii*) – 22.5% | 1.85 |

Butyric acid is produced by *Acetobacterium woodii*. This experiment shows that *Clostridium ljungdahlii* has the ability to convert butyric acid to butanol. If 100% of off gas from bioreactor Bi 120 is supplied to the bioreactor Bx 110, it is projected that specific butanol productivity is 8.2 g/L/g *Clostridium* cells/day.

Average carbon capture of the system was as follows.

| Reactor | % CO conversion | % CO2 conversion | % carbon conversion | % H2 conversion |
|---|---|---|---|---|
| Bioreactor 120 (*Clostridium ljungdahlii*) | 92 | N/A | 92 | 10 |
| Bioreactor 110 (*Acetobacterium woodii*) | 98 | 80 | 83 | 78 |
| Bioreactor 120 (*Clostridium ljungdahlii*) + Bioreactor 110 (*Acetobacterium woodii*) – 22.5% | 99.8 | 80 | 91 | 80 |

$CO_2$ is produced in bioreactor Bi 120 through the water-gas shift reaction.

While the disclosure herein disclosed has been described by means of specific embodiments, examples and applications thereof, numerous modifications and variations could be made thereto by those skilled in the art without departing from the scope of the disclosure set forth in the claims.

What is claimed is:

1. A process comprising:
providing a first gaseous substrate to a first bioreactor, the first gaseous substrate comprising $CO_2$ and containing about 5 to about 90 mole % $CO_2$ and about 0 to about 50 mole % CO;
providing a first acetogenic bacteria to the first bioreactor, wherein the first acetogenic bacteria includes a sodium translocating ATPase that is active during fermentation in the first bioreactor;
providing sodium ions to the first bioreactor through one or more sodium ion sources;
fermenting the first gaseous substrate with the first acetogenic bacteria in a fermentation broth comprising the first acetogenic bacteria and the one or more sodium ion sources to produce one or more organic acids, wherein the fermentation broth includes less than about 0.01 grams per liter yeast extract, less than about 0.01 grams per liter carbohydrate, wherein the sodium ions are provided with a sodium feed rate of about 290 to about 8750 μg/gram of cells/minute, and wherein the fermentation broth is maintained at a pH in a range of about 4 to about 6.9, wherein the fermenting of the first gaseous substrate with the first acetogenic bacteria provides about 50 to about 100% conversion of $CO_2$;
providing at least a portion of the one or more organic acids to a second bioreactor;

providing a second gaseous substrate to the second bioreactor, the second gaseous substrate comprising CO and containing about 5 to about 90 mole % CO;

providing a second acetogenic bacteria to the second bioreactor wherein the second acetogenic bacteria includes a proton translocating ATPase that is active during fermentation in the second bioreactor; and fermenting the second gaseous substrate in the second bioreactor with the second acetogenic bacteria in a fermentation broth comprising the second acetogenic bacteria to produce a liquid stream comprising one or more alcohols and a gaseous stream comprising $CO_2$, wherein at least a portion of the gaseous stream is provided to the first bioreactor.

2. The process of claim 1, wherein an additional stream comprising one or more organic acids is provided to the second bioreactor.

3. The process of claim 1, wherein the first gaseous substrate includes $H_2$.

4. The process of claim 1, wherein the first and second gaseous substrates are selected from the group consisting of industrial gases, fermentor gas streams and mixtures thereof.

5. The process of claim 1, wherein the first acetogenic bacteria is selected from the group consisting of *Acetobacterium* bacteria, Acetogeniuim *kivui, Acetoanaerobium noterae, Acetobacterium woodii, Alkalibaculum bacchi* CP11, *Moorella thermoacetica, Moorella thermoautotrophica, Ruminococcus productus, Acetogenium kivui*, and combinations thereof.

6. The process of claim 5, wherein the first acetogenic bacteria is *Acetobacterium woodii*.

7. The process of claim 1, wherein the sodium ion source is provided by a compound selected from the group consisting of sodium chloride, sodium hydroxide, sodium phosphate, sodium sulfate, sodium nitrate, sodium bicarbonate, sodium bisulfate and mixtures thereof.

8. The process of claim 1, wherein the organic acid is one or more C1 to C10 organic acid.

9. The process of claim 8, wherein the organic acid is acetic acid.

10. The process of claim 1, wherein the second acetogenic bacteria his selected from a group consisting of *Clostridium* bacteria, *Clostridium aceticum, Clostridium acetobutylicum, Clostridium acetobutylicum* P262 DSM 19630 of DSMZ Germany, *Clostridium autoethanogenum DSM* 19630 of DSMZ Germany, *Clostridium autoethanogenum* DSM 10061 of DSMZ Germany, *Clostridium autoethanogenum* DSM 23693 of DSMZ Germany, *Clostridium* autoethanogenum DSM 24138 of DSMZ Germany, *Clostridium carboxidivorans* P7 ATCC PTA-7827, *Clostridium coskatii* ATCC PTA-10522, *Clostridium drakei, Clostridium ljungdahlii* PETC ATCC 49587, *Clostridium ljungdahlii* ER12 ATCC 55380, *Clostridium ljungdahlii* C-01-ATCC 55988, *Clostridium ljungdahlii* O-52 ATCC 55889, *Clostridium magnum, Clostridium pasteurianum* DSM 325 of DSMZ Germany, *Clostridium* ragsdalei P11 ATCC BAA-622, *Clostridium scatologenes, Clostridium thermoaceticum, Clostridium ultunense*, acetogenic bacteria, *Acetobacterium* bacteria, *Acetogenium kivui, Acetoanaerobium noterae, Acetobacterium woodii, Alkalibaculum bacchi* CP11 ATCC BAA-1772, *Blautia producta, Butyribacterium methylotrophicum, Caldanaerobacter subterraneous, Caldanaerobacter subterraneous pacificus, Carboxydothermus hydrogenoformans, Desulfotomaculum kuznetsovii, Eubacterium limosum, Geobacter sulfurreducens, Methanosarcina acetivorans, Methanosarcina barkeri, Moorella thermoacetica, Moorella thermoautotrophica, Oxobacter pfennigii, Peptostreptococcus productus, Ruminococcus productus, Thermoanaerobacter kivui, Clostridium* Stick-*landii* and combinations thereof.

11. The process of claim 10, wherein the second acetogenic bacteria is *Clostridium ljungdahlii* C-01 ATCC 55984.

12. A process comprising:

providing a first gaseous substrate to a first bioreactor, the first gaseous substrate comprising $CO_2$ and $H_2$ and containing about 5 to about 90 mole % $CO_2$ and about 0 to about 50 mole % CO;

providing a first acetogenic bacteria to the first bioreactor, wherein the first acetogenic bacteria includes a sodium translocating ATPase that is active during fermentation in the first bioreactor;

providing sodium ions to the first bioreactor through one or more sodium ion sources;

fermenting the first gaseous substrate with the first acetogenic bacteria in a fermentation broth comprising the first acetogenic bacteria and the one or more sodium ion sources to produce one or more organic acids, wherein the fermentation broth includes less than about 0.01 grams per liter yeast extract, less than about 0.01 grams per liter carbohydrate, wherein the sodium ions are provided with a sodium feed rate of about 290 to about 8750 µg/gram of cells/minute, and wherein the fermentation broth is maintained at a pH in a range of about 4 to about 6.9, wherein the fermenting of the first gaseous substrate with the first acetogenic bacteria provides about 50 to about 100% conversion of $CO_2$;

providing at least a portion of the one or more organic acids to a second bioreactor;

providing a second gaseous substrate to the second bioreactor the second gaseous substrate comprising CO and containing about 5 to about 90 mole % CO;

providing a second acetogenic bacteria to the second bioreactor wherein the second acetogenic bacteria includes a proton translocating ATPase that is active during fermentation in the second bioreactor; and fermenting the second gaseous substrate in the second bioreactor with the second acetogenic bacteria in a fermentation broth comprising the second acetogenic bacteria to produce a liquid stream comprising one or more alcohols and a gaseous stream comprising $CO_2$, wherein at least a portion of the gaseous stream is provided to the first bioreactor.

13. The process of claim 12, wherein an additional stream comprising one or more organic acids is provided to the second bioreactor.

14. The process of claim 12, wherein the first and second gaseous substrates G are selected from the group consisting of industrial gases, fermentor gas streams and mixtures thereof.

15. The process of claim 12, wherein the first acetogenic bacteria is selected from the group consisting of *Acetobacterium* bacteria, *Acetogenium kivui, Acetoanaerobium noterae, Acetobacterium woodii, Alkalibaculum bacchi* CP11 ATCC BAA-1772, *Moorella thermoacetica, Moorella thermoautotrophica, Ruminococcus productus*, and combinations thereof.

16. The process of claim 15, wherein the first acetogenic bacteria is *Acetobacterium woodii*.

17. The process of claim 12, wherein the sodium ion source is provided by a compound selected from the group consisting of sodium chloride, sodium hydroxide, sodium phosphate, sodium sulfate, sodium nitrate, sodium bicarbonate, sodium bisulfate and mixtures thereof.

18. The process of claim 12, wherein the organic acid is one or more C1 to C10 organic acid.

19. The process of claim 18, wherein the organic acid is acetic acid.

20. The process of claim 12, wherein the second acetogenic bacteria his selected from a group consisting of *Clostridium* bacteria,

*Clostridium aceticum, Clostridium acetobutylicum, Clostridium acetobutylicum* P262 DSM 19630 of DSMZ Germany, *Clostridium autoethanogenum* DSM 19630 of DSMZ Germany, *Clostridium autoethanogenum* DSM 10061 of DSMZ Germany, *Clostridium autoethanogenum* DSM 23693 of DSMZ Germany), *Clostridium* autoethaniogenum DSM 24138 of DSMZ Germany, *Clostridium carboxidivorans* P7 ATCC PTA-7827, *Clostridium* coskatii ATCC PTA-10522, *Clostridium drakei, Clostridium ljungdahlii* PETC ATCC 49587, *Clostridium ljungdahlii* ER12 ATCC 55380, *Clostridium ljungdahlii* C-01-ATCC 55988, *Clostridium ljungdahlii* O-52 ATCC 55889, *Clostridium magnum, Clostridium pasteurianum* DSM 325 of DSMZ Germany), *Clostridium* ragsdalei P11 ATCC BAA-622, *Clostridium scatologenes, Clostridium thermoaceticum, Clostridium ultunense*, acetogenic bacteria, *Acetobacterium* bacteria, *Acetogenium kivui, Acetoanaerobium noterae, Acetobacterium woodii, Alkalibaculum bacchi* CP11 ATCC BAA-1772, *Blautia producta, Butyribacterium methylotrophicum, Caldanaerobacter subterraneous, Caldanaerobacter subterraneous pacificus, Carboxydothermus hydrogenoformans, Desulfotomaculum kuznetsovii, Eubacterium limosum, Geobacter sulfurreducens, Methanosarcina acetivorans, Methanosarcina barkeri, Moorella thermoacetica, Moorella thermoautotrophica, Oxobacter pfennigii, Peptostreptococcus productus, Ruminococcus productus, Thermoanaerobacter kivui*, and combinations thereof.

21. The process of claim 20, wherein the second acetogenic bacteria is *Clostridium ljungdahlii* C-01 ATCC 55988.

* * * * *